United States Patent
Khan et al.

(10) Patent No.: US 10,786,683 B2
(45) Date of Patent: Sep. 29, 2020

(54) LIGHT-EMITTING DEVICES FOR WOUND HEALING

(71) Applicants: Nitto Denko Corporation, Osaka (JP); The Henry M. Jackson Foundation for the Advancement of Military Medicine, Inc., Bethesda, MD (US)

(72) Inventors: Sazzadur Rahman Khan, San Diego, CA (US); Sheng Li, Vista, CA (US); Amane Mochizuki, Osaka (JP); Xingjia Wu, Germantown, MD (US); Juanita Josephine Anders, Potomac, MD (US)

(73) Assignees: Nitto Denko Corporation, Osaka (JP); The Henry M. Jackson Foundation for the Advancement of Military Medicine, Inc., Bethesda, MD (US)

(*) Notice: Subject to any disclaimer, the term of this patent is extended or adjusted under 35 U.S.C. 154(b) by 0 days.

(21) Appl. No.: 15/015,923

(22) Filed: Feb. 4, 2016

(65) Prior Publication Data
US 2016/0236007 A1    Aug. 18, 2016

Related U.S. Application Data

(63) Continuation of application No. 13/649,277, filed on Oct. 11, 2012, now abandoned.
(Continued)

(51) Int. Cl.
*A61M 37/00* (2006.01)
*A61N 5/06* (2006.01)

(52) U.S. Cl.
CPC ......... *A61N 5/0616* (2013.01); *A61N 5/062* (2013.01); *A61N 5/0624* (2013.01);
(Continued)

(58) Field of Classification Search
CPC ......... H01L 35/24; H05B 33/00; A61B 18/18; A61N 5/06; A61N 2005/0645;
(Continued)

(56) References Cited

U.S. PATENT DOCUMENTS

| 5,616,140 A | 4/1997 | Prescott |
| 6,387,089 B1 | 5/2002 | Kreindel et al. |

(Continued)

FOREIGN PATENT DOCUMENTS

| EP | 1430850 A2 | 6/2004 |
| WO | WO2010-039886 | 4/2010 |
| WO | WO2011-069590 | 6/2011 |

OTHER PUBLICATIONS

Byrnes, Kimberly R. et al., "Photobiomodulation improves cutaneous wound healing in an animal model of type II diabetes", Photomedicine and Laser Surgery, vol. 22, No. 4, Jan. 1, 2004, pp. 281-290.

*Primary Examiner* — Jon Eric C Morales
(74) *Attorney, Agent, or Firm* — K&L Gates LLP; Louis C. Cullman; Hal Gibson

(57) ABSTRACT

Methods and devices related to wound healing using phototherapy are described. Some embodiments provide an organic light-emitting diode device, such as a light-emitting device for phototherapy, comprising Ring System 1, Ring System 2, Ring System 3, Ring System 4 or Ring System 5.

13 Claims, 17 Drawing Sheets

Related U.S. Application Data

(60) Provisional application No. 61/547,267, filed on Oct. 14, 2011.

(52) U.S. Cl.
CPC .............. *A61N 2005/063* (2013.01); *A61N 2005/0627* (2013.01); *A61N 2005/0645* (2013.01); *A61N 2005/0653* (2013.01); *A61N 2005/0662* (2013.01)

(58) Field of Classification Search
CPC .... A61N 5/0616; A61N 5/062; A61N 5/0624; A61N 2005/0627; A61N 2005/063; A61N 2005/0653; A61N 2005/0662; C09K 11/06; C09K 2211/1007; C09K 2211/1011; C09K 2211/1014; C09K 2211/1044; C07D 235/18; C07D 403/10; A61M 37/00; Y10S 428/917
USPC ........ 257/40; 313/504; 606/9, 4, 10; 607/88, 607/91; 602/42; 428/690; 604/20
See application file for complete search history.

(56) References Cited

U.S. PATENT DOCUMENTS

| | | | |
|---|---|---|---|
| 6,538,375 B1 | 3/2003 | Duggal et al. | |
| 6,866,678 B2 | 3/2005 | Shenderova et al. | |
| 7,479,136 B2 | 1/2009 | Dotson | |
| 7,843,125 B2 | 11/2010 | Smith et al. | |
| 7,887,533 B2 | 2/2011 | Barolet et al. | |
| 8,003,229 B2 | 8/2011 | Sisk et al. | |
| 8,192,473 B2 | 6/2012 | Tucker et al. | |
| 8,426,040 B2 * | 4/2013 | Zheng | C07D 235/18 313/504 |
| 8,929,978 B2 * | 1/2015 | Khan | A61N 5/062 257/40 |
| 8,933,243 B2 * | 1/2015 | Zheng | C07D 235/18 548/310.7 |
| 9,373,797 B2 * | 6/2016 | Zheng | C07D 235/18 |
| 9,548,458 B2 * | 1/2017 | Zheng | C07D 235/18 |
| 2005/0080465 A1 | 4/2005 | Zelickson et al. | |
| 2006/0217690 A1 | 9/2006 | Bastin et al. | |
| 2007/0161625 A1 | 7/2007 | Brown et al. | |
| 2007/0248841 A1 * | 10/2007 | Hosokawa | C09K 11/06 428/690 |
| 2008/0058689 A1 | 3/2008 | Holloway et al. | |
| 2009/0039290 A1 | 2/2009 | Prakash et al. | |
| 2010/0010593 A1 | 1/2010 | Wagennar Cacciola et al. | |
| 2010/0016844 A1 | 1/2010 | Patel, Jr. | |
| 2010/0082081 A1 | 4/2010 | Niessen et al. | |
| 2010/0106077 A1 | 4/2010 | Rabin et al. | |
| 2010/0179469 A1 | 7/2010 | Hammond et al. | |
| 2010/0301741 A1 | 12/2010 | Kim et al. | |
| 2011/0140093 A1 * | 6/2011 | Zheng | C07D 235/18 257/40 |
| 2011/0144410 A1 | 6/2011 | Kennedy | |
| 2011/0251401 A1 * | 10/2011 | Zheng | C07D 235/18 548/305.1 |
| 2012/0197179 A1 * | 8/2012 | Khan | A61N 5/062 604/20 |

\* cited by examiner

|   | Mean ±SEM | | P value |
|---|---|---|---|
| OLED | 1.049±0.037 | N=12 | 0.1776 |
| Laser | 1.156±0.075 | N=8 | |

ED1 immuniohistochemisty

LIGHT-EMITTING DEVICES FOR WOUND HEALING

CROSS-REFERENCE TO RELATED APPLICATIONS

This application is a continuation of U.S. application Ser. No. 13/649,277, filed Oct. 11, 2012, which claims the benefit of U.S. Provisional Patent Application No. 61/547,267, filed Oct. 14, 2011. Each of these disclosures, which is incorporated by reference herein in its entirety.

BACKGROUND

Wound healing is impaired in some individuals, such as patients suffering from certain disorders such as diabetes. This impairment in wound healing often leads to chronic wounds, the ongoing treatment of which represents a significant medical burden. Phototherapy can be useful in wound healing. However, available light sources that can be used for phototherapy, such as lasers, can be expensive, difficult to transport, and otherwise not suitable for home or outpatient treatment. Therefore, there is a need for alternative light sources for phototherapy.

SUMMARY

Some embodiments include a light-emitting device for use in phototherapy comprising: a light-emitting layer comprising a luminescent compound that has a peak emission of about 600 nm to about 700 nm, wherein the device is configured to provide an amount of light from the light-emitting layer effective to treat a wound of a mammal. Some embodiments include a light-emitting device for use in phototherapy comprising: a light-emitting layer comprising a luminescent compound that has a peak emission of about 620 nm to about 640 nm, wherein the device is configured to provide an amount of light from the light-emitting layer effective to treat a wound of a mammal. In further embodiments, the device is configured provide light to the wound at a power density of about 2 mW/cm$^2$ to about 20 mW/cm$^2$. In other embodiments, the device is configured provide light to the wound at a power density of about 7 mW/cm$^2$ to about 10 mW/cm$^2$.

In some embodiments, the light-emitting device further comprises a dosage component configured to deliver a dose of about 0.1 J/cm$^2$ to about 10 J/cm$^2$ to a wound of a human being. In some embodiments, the dosage component comprises a timer coupled to a positioning component.

In some embodiments of the present disclosure the light-emitting device comprises a flexible substrate, which comprises an organic light-emitting diode (OLED) coupled to the flexible substrate, wherein the light emitting diode comprises the light-emitting layer disposed between an anode and a cathode.

Further embodiments relate to a phototherapy system, which comprises a light-emitting device as disclosed above and a wound dressing. In some embodiments, the phototherapy system further comprises a dosage component that is configured to deliver a dose of about 0.05 J/cm$^2$ to about 15 J/cm$^2$ to a wound of a human being. In certain embodiments, the dosage component is configured to deliver a dose of about 0.2 J/cm$^2$ to about 5 J/cm$^2$ to the wound of the human being.

Some embodiments of the present disclosure relate to methods of treating a wound, comprising exposing at least a portion of the wound to light from a light-emitting device or system as disclosed herein. In certain embodiments, the methods relate to treating a wound of a human being with diabetes.

These and other embodiments are described in greater detail below.

BRIEF DESCRIPTION OF THE DRAWINGS

FIG. 21A shows wound closure daily measurements, with the value for each flank wound treated with light therapy (LT) normalized to its corresponding untreated control flank. FIG. 21B shows area under the curve measurements.

FIG. 24C shows the quantification of positive labeling of OLED and control groups (***p<0.001).

FIG. 25C shows the quantification of positive label of control of OLED-treated groups (*p<0.05).

DETAILED DESCRIPTION

Devices

The term "work function" has the ordinary meaning known to one of ordinary skill in the art. For example, the "work function" of a metal may refer to a measure of the minimum energy required to extract an electron from the surface of the metal.

The term "high work function metal" has the ordinary meaning known to one of ordinary skill in the art, and includes a metal or alloy that easily injects holes and typically has a work function greater than or equal to 4.5.

The term "low work function metal" has the ordinary meaning known to one of ordinary skill in the art, and includes a metal or alloy that easily loses electrons and typically has a work function less than 4.3.

Some light-emitting devices may comprise an organic component disposed between an anode and a cathode. An organic component may comprise one or more layers comprising organic materials. Examples of such layers may include an emissive layer, a hole-transport layer, an electron-transport layer, a hole-injection layer, an electron injection layer, etc.

Figure 1:
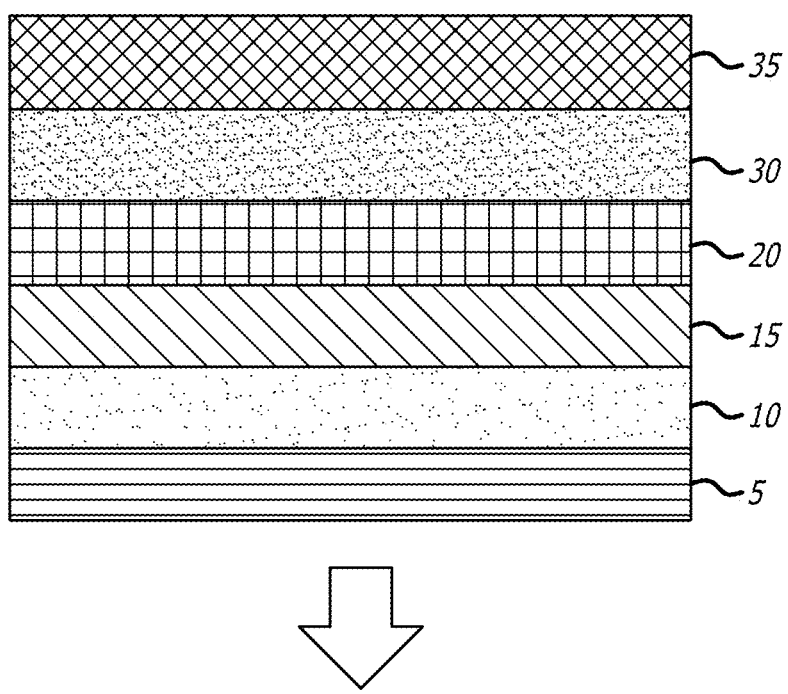
FIG. 1 is a schematic diagram of an embodiment of a bottom emissive device.

Some organic light-emitting diode (OLED) devices comprising a compound described herein may be schematically represented in FIG. 1. Such a device comprises the following layers in the order given: an anode 5, a hole-injection layer 10, a hole-transport layer 15, a light-emitting layer 20, an electron-transport layer 30, and a cathode 35. A capping layer and/or an enhancement layer may be disposed on cathode 35.

Figure 2:
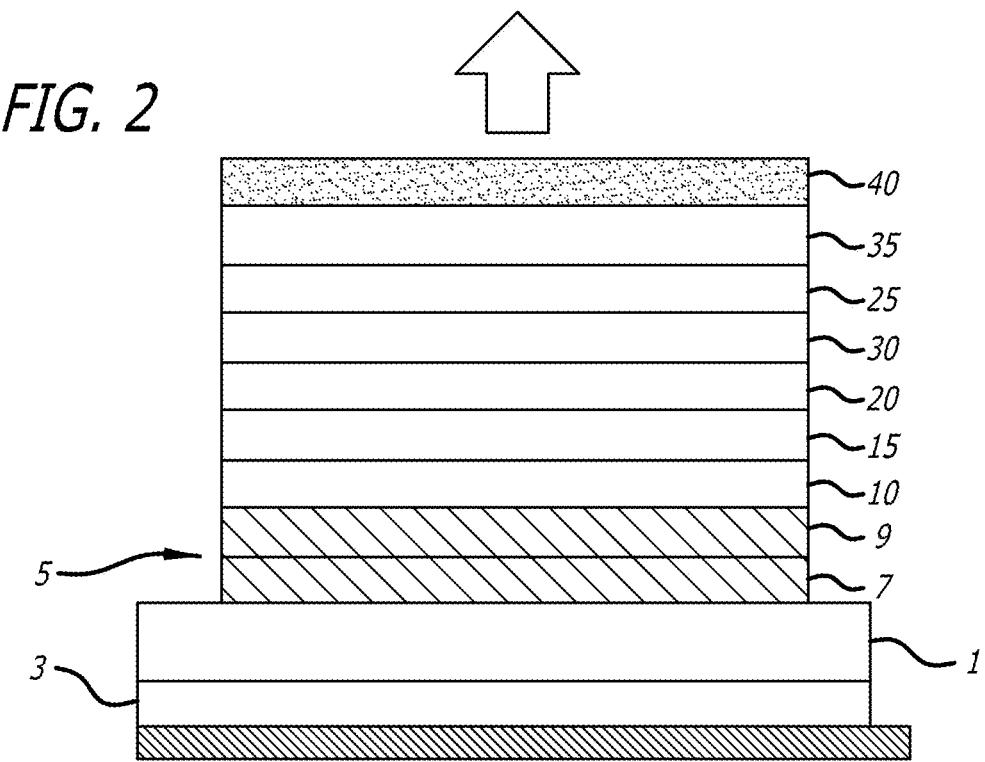
FIG. 2 is a schematic diagram of an embodiment of a top emissive device.

Some OLED devices may have a structure represented schematically by FIG. 2. A light-emitting layer 20 is disposed between an anode 5 and cathode 35. The anode 5 may comprise two anode sublayers: a first anode sublayer 7, and a second anode sublayer 9 disposed between the first anode sublayer 7 and the light-emitting layer 20. An optional electron-transport layer 30 may be disposed between the light-emitting layer 20 and the cathode 35, the second cathode sublayer 38, or the electron-injecting layer 25. An optional hole-injecting layer 10 may be disposed between the light-emitting layer 20 and the anode 5 or the second anode sublayer 9. An optional hole-transport layer 15 may be disposed between the hole-injecting layer 10 and the light-emitting layer 20. The anode 5 may optionally be disposed on a substrate 1, and the substrate 1 may optionally be disposed on a heat dissipation layer 3. A capping layer 40 may optionally be disposed on the cathode 35. In some embodiments, an enhancement layer (not shown) may be disposed on capping layer 40.

An anode layer, e.g. anode 5, may comprise a conventional material such as a metal, mixed metal, alloy, metal oxide or mixed-metal oxide, or a conductive polymer. Examples of suitable metals include Group 10, Group 11, and Group 12 transition metals. If the anode layer is to be light-transmitting, mixed-metal oxides of Groups 12, Group 13, and Group 14 metals or alloys thereof, such as zinc oxide, tin oxide, indium zinc oxide (IZO) or indium-tin-oxide (ITO) may be used. The anode layer may include an organic material such as polyaniline, e.g., as described in "Flexible light-emitting diodes made from soluble conducting polymer," Nature, vol. 357, pp. 477-479 (11 Jun. 1992), which is incorporated by reference herein. Examples of suitable high work function metals include but are not limited to Au, Pt, indium-tin-oxide (ITO), or alloys thereof. In some embodiments, the anode layer can have a thickness in the range of about 1 nm to about 1000 nm.

A first anode sublayer, e.g. first anode sublayer 7 may comprise Al, Ag, Ni, or a combination thereof. The thickness of a first anode sublayer may vary. For example, a first anode sublayer may have thickness of: about 10 nm to about 100 nm, about 10 nm to about 70 nm, about 40 nm to about 60 nm, about 10 nm, about 50 nm, about 70 nm, about 100 nm, or any thickness in a range defined by, or between, any of these values.

A second anode sublayer, e.g. second anode sublayer 9 may comprise Al, Ag, Au, or a combination thereof. The thickness of a second anode sublayer may also vary. For example, a second anode sublayer may have a thickness of: about 5 nm to about 200 nm, about 10 nm to about 100 nm, about 30 nm to about 70 nm, about 25 nm, about 40 nm, about 50 nm, to about 200 nm, or any thickness in a range defined by, or between, any of these values.

In some embodiments, a first anode sublayer may comprise Al and/or a second anode sublayer may comprise Ag.

A cathode layer, e.g. cathode 35, may include a material having a lower work function than the anode layer. Examples of suitable materials for the cathode layer include those selected from alkali metals of Group 1, Group 2 metals, Group 11, Group 12, and Group 13 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, one or more metals, such as Ag and Mg may be co-deposited. In some embodiments, a cathode may comprise two cathode sublayers: a first cathode sublayer, and a second cathode sublayer disposed between the first cathode sublayer and the light-emitting layer. In some embodiments, the cathode layer can have a thickness in the range of about 1 nm to about 1000 nm.

A first cathode sublayer may comprise alkali metals of Group 1, Group 2 metals, Group 12 metals including rare earth elements, lanthanides and actinides, materials such as aluminum, indium, calcium, barium, samarium and magnesium, and combinations thereof. In some embodiments, a first cathode sublayer comprises Al, Ag, Au, Cu, Mg/Ag, or alloys thereof.

The thickness of a first cathode sublayer may vary. For example, a first cathode sublayer may have a thickness of about 0.1 nm, about 1 nm, about 2 nm, about 4 nm, about 5 nm, about 6 nm, about 10 nm, about 12 nm, about 16 nm, about 20 nm, about 50 nm, or any thickness in a range defined by, or between, any of these values. In some embodiments, a second cathode sublayer may have a thickness of about 0.1 nm to about 50 nm, about 1 nm to about 20 nm, about 5 nm to about 20 nm, or about 16 nm.

A second cathode sublayer may comprise alkali metals of Group 1, Group 2 metals, Group 12 metals including rare earth elements, lanthanides and actinides, materials such as aluminum, indium, calcium, barium, samarium and magnesium, and combinations thereof. In some embodiments, a second cathode sublayer comprises Mg, Ca, Mg/Ag, LiF/Al, CsF, CsF/Al or alloys thereof.

The thickness of a second cathode sublayer may vary. For example, a second cathode sublayer may have thickness of about 0.1 nm to about 50 nm, about 0.1 nm to about 10 nm, about 0.5 nm to about 2 nm, about 0.1 nm, about 1 nm, about 2 nm, about 4 nm, about 5 nm, about 6 nm, about 10 nm, about 12 nm, about 20 nm, about 50 nm, or any thickness in a range defined by, or between, any of these values.

In some embodiments, a first cathode sublayer comprises Mg/Ag and/or a second cathode sublayer comprises Mg. In some embodiments, a first cathode sublayer is about 16 nm thick and/or a second cathode sublayer is about 1 nm thick.

A light-emitting layer, e.g. light-emitting layer 20, may comprise a light-emitting component, and optionally, a host. For example, a light-emitting layer may consist essentially of a light-emitting component. Alternatively, a light-emitting layer may comprise a light-emitting component and other components such as a host. A host may comprise a hole-transport material, an electron-transport material, and/or an ambipolar material. In some devices, a light emitting component may be about 0.1% to about 10%, about 1% to about 5%, or about 3% of the mass of the light-emitting layer.

In some embodiments, a host may be HOST-1, HOST-2, HOST-3, HOST-4, HOST-5, HOST-6, HOST-7, HOST-8, or HOST-9.

HOST-1

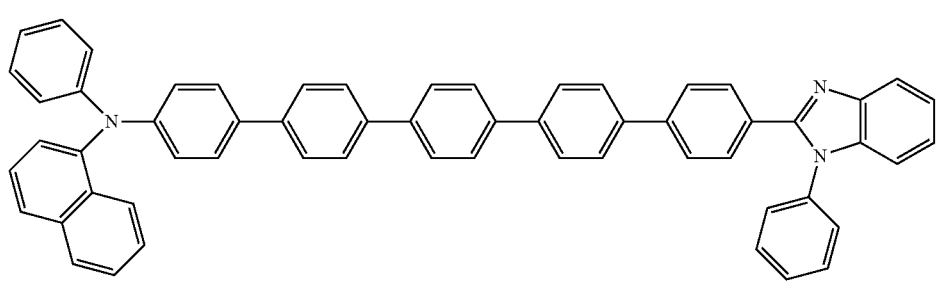

HOST-2

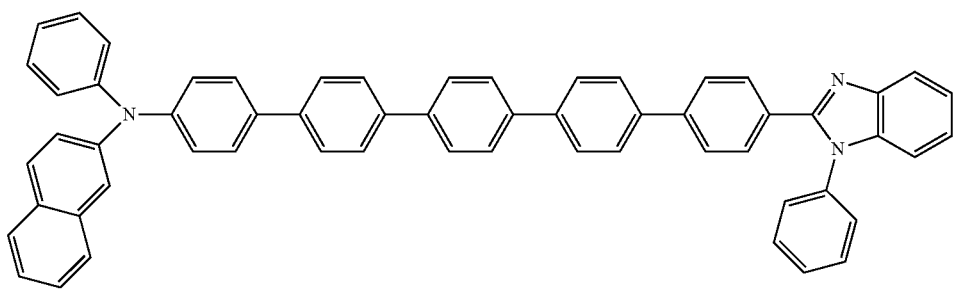

HOST-3

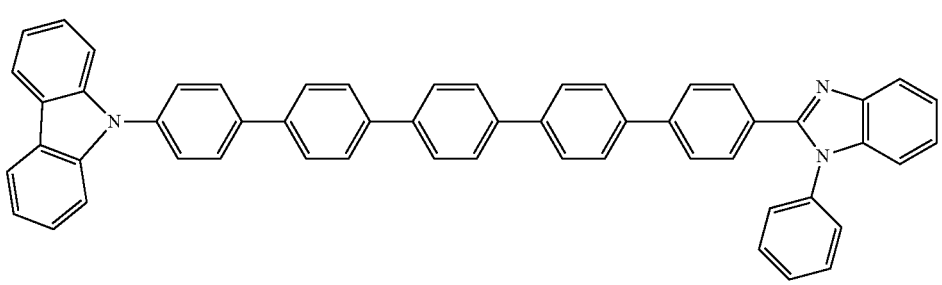

HOST-4

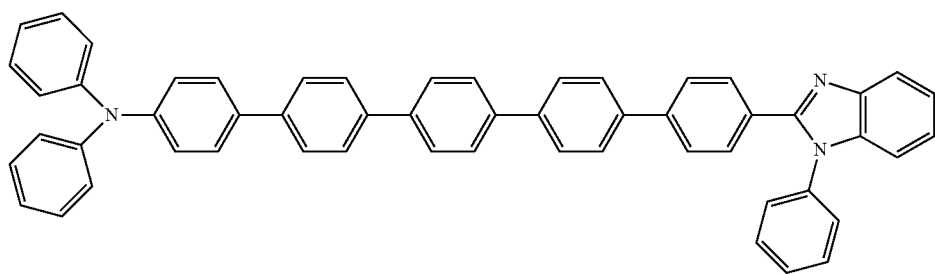

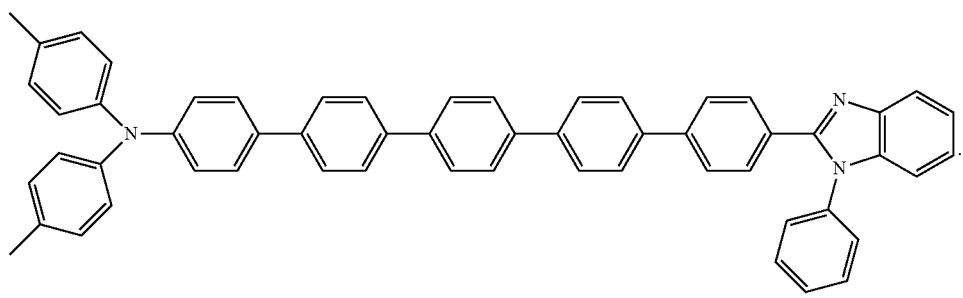

HOST-5

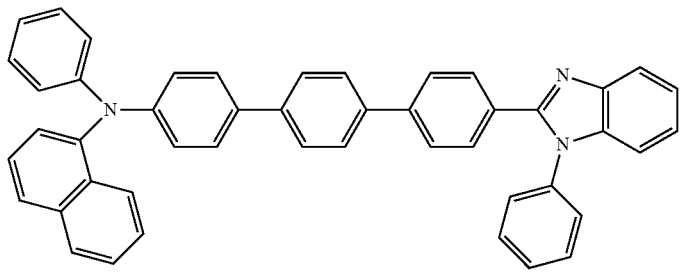

HOST-6

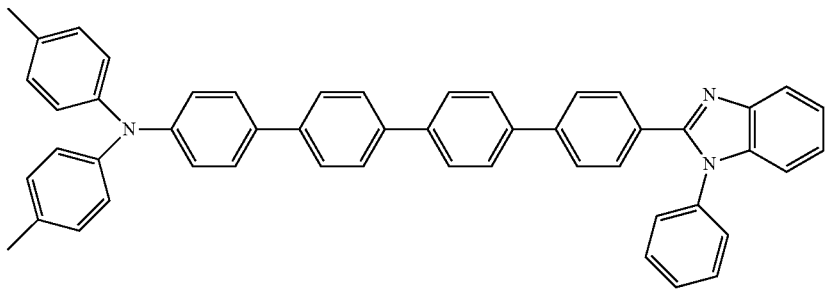

HOST-7

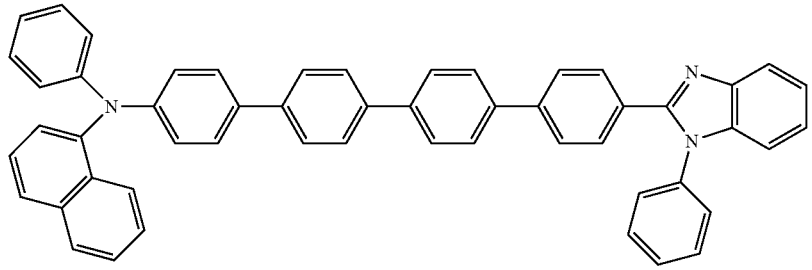

HOST-8

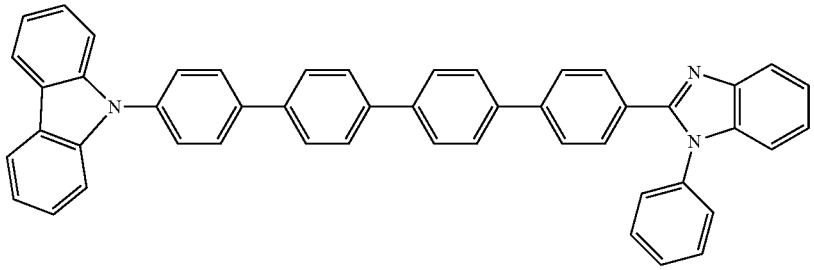

HOST-9

Other hosts may include, but are not limited to, compounds described in U.S. Pat. No. 8,003,229, issued on Aug. 23, 2011, which is incorporated by reference in its entirety, especially the disclosure related to compounds of Formulas 1-3. Other useful hosts include those described in co-pending patent application Ser. No. 13/033,473, filed Feb. 23, 2011 and co-pending patent application Ser. No. 13/166,246, filed Jun. 22, 2011, both of which are incorporated by reference herein in their entireties. Other useful hosts include those described in US 2012/0197179, published on Aug. 12, 2012, which is incorporated by reference in its entirety, especially the disclosure related to optionally substituted ring systems: Ring system 1, Ring system 2, Ring system 3, and Ring system 4.

If a host is present, the amount of a host in a light-emitting layer may vary. In one embodiment, the amount of a host in a light-emitting layer may be in the range of from about 1% to nearly 100% by weight of the light-emitting layer. In another embodiment, the amount of a host in a light-emitting layer may be about 90% to about 99% by weight, or about 97% by weight, of the light-emitting layer.

A light-emitting component may be a fluorescent and/or a phosphorescent compound. In some embodiments, the light-emitting component comprises a phosphorescent material.

Some non-limiting examples of compounds which may form part or all of a light-emitting component include iridium coordination compounds such as: bis[2-(2'-benzothienyl)-pyridinato-N,C3']iridium (III)(acetylacetonate); bis[(2-phenylquinolyl)-N,C2']iridium (III) (acetylacetonate); bis[(1-phenylisoquinolinato-N,C2')]iridium (III) (acetylacetonate); bis[(dibenzo[f, h]quinoxalino-N,C2')iridium (III) (acetylacetonate); tris(2,5-bis-2'-(9',9'-dihexylfluorene)pyridine)iridium (III); tris[1-phenylisoquinolinato-N,C2'] iridium (III); tris-[2-(2'-benzothienyl)-pyridinato-N,C3'] iridium (III); tris[1-thiophen-2-ylisoquinolinato-N,C3'] iridium (III); and tris[1-(9,9-dimethyl-9H-fluoren-2-yl) isoquinolinato-(N,C3')iridium (III)), etc.

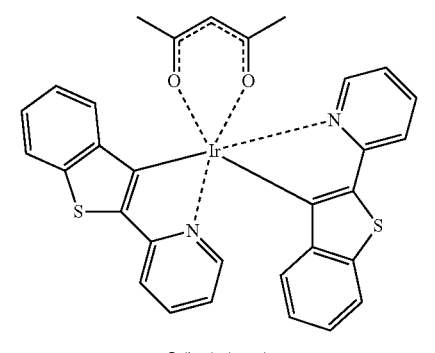

1

Ir(btp)₂(acac)

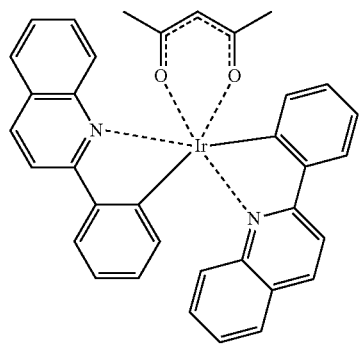

2

Ir(pq)₂(acac)

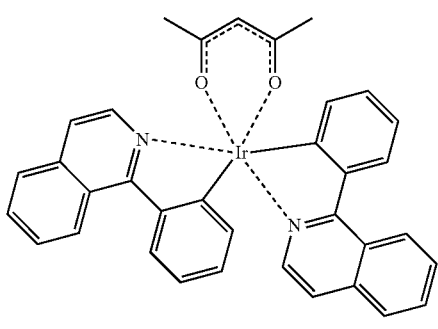

3

Ir(piq)₂(acac)

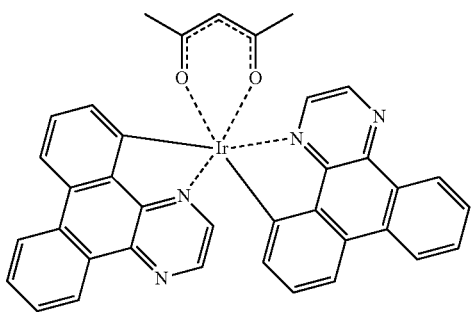

4

Ir(DBQ)₂(acac)

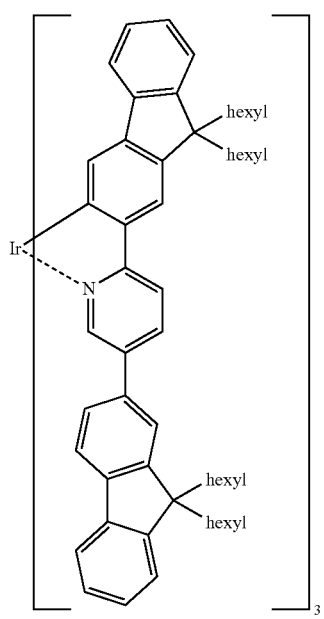

5

Ir(HFP)₃

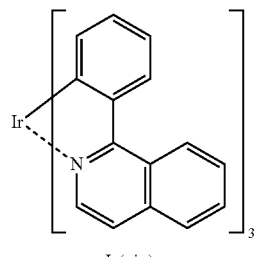

6

Ir(piq)₃

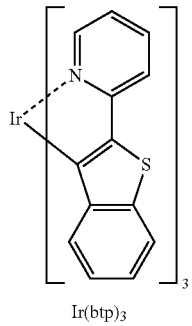

7

Ir(btp)₃

-continued

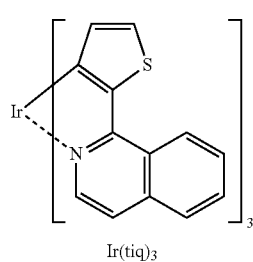

Ir(tiq)₃

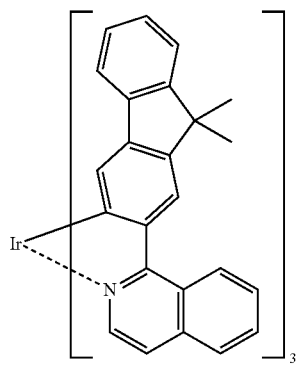

Ir(fli1)₃

1. (Btp)₂Ir(III)(acac); bis[2-(2'-benzothienyl)-pyridinato-N,C3'] iridium(III) (acetylacetonate)
2. (Pq)₂Ir(III)(acac); bis[(2-phenylquinolyl)-N,C2']iridium (III) (acetylacetonate)
3. (Piq)₂Ir(III)(acac); bis[(1-phenylisoquinolinato-N,C2')]iridium (III) (acetylacetonate)
4. (DBQ)₂Ir(acac); bis[(dibenzo[f, h]quinoxalino-N,C2')iridium (III)(acetylacetonate)
5. [Ir(HFP)₃], tris(2,5-bis-2'-(9',9'-dihexylfluorene)pyridine)iridium (III)
6. Ir(piq)₃; tris[1-phenylisoquinolinato-N,C2']iridium (III)
7. Ir(btp)₃; tris-[2-(2'-benzothienyl)-pyridinato-N,C3'] iridium (III)
8. Ir(tiq)₃, tris[1-thiophen-2-ylisoquinolinato-N,C3']iridium (III)
9. Ir(fliq)₃; tris[1-(9,9-dimethyl-9H-fluoren-2-yl)isoquinolinato-(N,C3')iridium (III))

The thickness of the light-emitting layer may vary. In some embodiments, the light-emitting layer may have a thickness in the range of from about 5 nm to about 200 nm or about 10 nm to about 150 nm.

Some devices may be configured so that holes can be transferred from the anode to a light-emitting layer and/or so that electrons can be transferred from the cathode to a light-emitting layer.

A hole-transport layer, e.g. hole-transport layer 15, may be disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly (9-vinylcarbazole); polyfluorene; a polyfluorene copolymer; poly(9, 9-di-n-octylfluorene-alt-benzothiadiazole); poly (paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-bis(4-bis(4-methylphenyl)aminophenyl)cyclohexane; 2,9-Dimethyl-4,7-diphenyl-1, 10-phenanthroline; 3,5-bis(4-tert-butyl-phenyl)-4-phenyl[1,2,4]triazole; 3,4,5-triphenyl-1,2,3-triazole; 4,4',4'-tris(3-methylphenylphenylamino)triphenylamine (MTDATA); N, N'-bis(3-methylphenyl)N,N'-diphenyl-[1,1'-biphenyl]-4,4'-diamine (TPD); 4,4'-bis[N-(naphthyl)-N-phenyl-amino]biphenyl (NPB); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); bis [4-(p,p'-ditolyl-amino)phenyl]diphenylsilane (DTASi); 2,2'-bis(4-carbazolylphenyl)-1,1'-biphenyl (4CzPBP); N,N'N"-1, 3,5-tricarbazoloylbenzene (tCP); N,N'-bis(4-butylphenyl)-N,N'-bis(phenyl)benzidine; or the like.

A hole-injection layer, e.g. hole-injecting layer 10, may be disposed between the light-emitting layer and the anode. Various suitable hole-injection materials that can be included in the hole-injection layer are known to those skilled in the art. Examples of hole-injection material(s) include MoO₃, V₂O₅, WO₃, or an optionally substituted compound selected from the following: a polythiophene derivative such as poly(3,4-ethylenedioxythiophene) (PEDOT)/polystyrene sulphonic acid (PSS), a benzidine derivative such as N,N,N',N'-tetraphenylbenzidine, poly(N,N'-bis (4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino) triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthioacetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials. A p-doped hole injecting layer may include a hole injecting material doped with a hole-transport material, for example a p-doped hole injecting layer may comprise MoO₃ doped with NPB.

An electron-transport layer, e.g. electron-transport layer 30, may be disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-tert-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis [2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate (Alq₃), phenanthroline, quinoxaline, 1,3,5-tris[N-phenylbenzimidazol-z-yl]benzene (TPBI), or a derivative or a combination thereof.

In some embodiments, the light-emitting device can include an electron injection layer, e.g. electron injecting layer 25, between the cathode layer and the light-emitting layer. In some embodiments, the lowest unoccupied molecular orbital (LUMO) energy level of the electron injection material(s) may be high enough to prevent it from receiving an electron from the light-emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above, or a derivative or a combination thereof.

A substrate, e.g. substrate 1, may be any material, such as a glass or a metal, upon which the light-emitting diode may be mounted.

A heat dissipation layer, e.g., the heat dissipation layer 3, includes any layer of material that may be capable of increasing the surface area of the device for thermal exchange, spreading the heat uniformly throughout the device area, transferring the heat to the heat sink materials, and/or releasing the heat outside of the device. A typical heat dissipation layer may include, but is not limited to: an aluminum sheet with a fin structure, aluminum tape with thermal conductive adhesive, a copper thin film, a graphite sheet, a stainless steel film, a Si-wafer, a thin film of boron nitride, a thermal conductive grease, a gel, or combinations of above.

An enhancement layer may be any layer that improves the efficiency of the emission of light from an OLED device or reduces variation in emission with viewing angle. An enhancement layer may enhance emission by about 1.1 times to about 3 times or about 1.5 times to about 1.8 times, as compared to a similar device having no enhancement layer. Examples of such materials may include, but are not limited to, transparent materials including organic small molecule materials such as NPB, TPBI, Alq3; metal oxides such as $MoO_3$, $WO_3$, $SnO_2$ and SnO; wide band gap semiconductor compounds; etc. An enhancement layer may be in the form of nanostructures or microstructures or may be a nanoporous or microporous layer. Additional examples include enhancement layers and/or porous films as described in US Patent Application Publication 20120223635, entitled, "POROUS FILMS FOR USE IN LIGHT-EMITTING DEVICES," which is herein incorporated by reference in its entirety. An enhancement layer may have a thickness of about 100 nm to about 10 μm, about 500 nm to about 5 μm, or about, about 50 nm to about 100 nm, about 60 nm, about 80 nm, or any thickness in a range bounded by, or between, any of these values.

A capping layer, e.g. capping layer 40, may be any layer that improves the efficiency of the emission of light from an OLED device or reduces variation in emission with viewing angle. In some embodiments, a capping layer may be a material that is more suitable for deposition on the cathode than material of an enhancement layer. Thus, a capping layer disposed on a cathode may allow an enhancement layer to be disposed on the capping layer. Examples of capping layer materials may be similar to those of enhancement layers, such a transparent materials including organic small molecule materials such as NPB, TPBI, Alq3; metal oxides such as $MoO_3$, $WO_3$, $SnO_2$ and SnO; wide band gap semiconductor compounds; etc. Additional examples include enhancement layers and/or porous films as described in US Patent Application Publication 20120223635, entitled, "POROUS FILMS FOR USE IN LIGHT-EMITTING DEVICES," which is herein incorporated by reference in its entirety. In some embodiments, a capping layer may be NPB. A capping layer may have a thickness of about 100 nm to about 10 μm, about 500 nm to about 5 μm, or about, about 50 nm to about 100 nm, about 60 nm, about 80 nm, or any thickness in a range bounded by, or between, any of these values.

If desired, additional layers may be included in the light-emitting device. These additional layers may include a hole-blocking layer (HBL) and/or an exciton-blocking layer (EBL). In addition to separate layers, some of these materials may be combined into a single layer.

If present, a hole-blocking layer may be between a cathode and a light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

If present, an exciton-blocking layer may be between a light-emitting layer and an anode. In an embodiment, the band gap of the material(s) that comprise an exciton-blocking layer may be large enough to substantially prevent the diffusion of excitons. A number of suitable exciton-blocking materials that can be included in an exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (NPB), 4,4'-N,N'-dicarbazole-biphenyl (CBP), and bathocuproine (BCP), and any other material(s) that have a large enough band gap to substantially prevent the diffusion of excitons.

Light-emitting devices disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least a compound disclosed herein, and an optional electroluminescent compound, can be deposited on the anode. A cathode layer, comprising a low work functioning metal (e.g., Mg:Ag), can then be deposited, e.g. vapor evaporated, onto the light-emitting layer. If desired, the device can also include an electron-transport/injection layer, a hole-blocking layer, a hole-injection layer, an exciton-blocking layer and/or a second light-emitting layer that can be added to the device using techniques known in the art, as informed by the guidance provided herein. See also the Examples that follow for certain embodiments of the present disclosure.

Phototherapy

Devices disclosed herein may be useful in phototherapy. Typically, phototherapy involves exposing at least a portion of the tissue of a mammal to light, such as light from a device described herein. For example, at least a portion of light emitted from a device described herein may come in contact with a mammal, such as a human being. The light from the device that comes in contact with the mammal may then provide a therapeutic effect to the mammal through a variety of mechanisms, some of which are explored later in this document.

A device may be configured to emit an effective amount of light to provide a therapeutic effect to a mammal. A therapeutic effect includes any detectable diagnosis, cure, mitigation, treatment, or prevention of disease, or other effect on the structure or function of a mammal's body. Some examples of conditions that phototherapy may be useful to treat or diagnose include, but are not limited to, wounds, such as wounds on a diabetic human being, infection, cancer/tumors, cardiovascular conditions, dermatological or skin conditions, a condition affecting the eye, obesity, pain or inflammation, conditions related to immune response, etc.

The color of the light used for phototherapy may vary according to the particular treatment, the absorption spectrum of any photosensitive compounds, and other factors. For example, light in the red to ultraviolet range may be useful for penetrating tissue. Visible red wavelengths may accelerate wound healing in diabetic animals and human beings. In some embodiments, an OLED used in phototherapy may have peak emission or an median emission (e.g., the wavelength having equal areas in the visible spectra higher and lower than the wavelength) at a wavelength of about 620 nm to about 640 nm, about 625 nm to about 635 nm, about 630 nm, about 635 nm, or any wavelength in a range bounded by, or between, any of these values.

The light itself may be at least partially responsible for the therapeutic effects of the phototherapy, thus phototherapy may be carried out without a photosensitive compound.

The light may also be used in conjunction with a photosensitive compound. The photosensitive compound may be administered directly or indirectly to body tissue so that the photosensitive compound is in or on the tissue. Since the photosensitive compound is in or on the tissue, at least a portion of the photosensitive compound may be exposed to light emitted from the device and directed toward or through the tissue. The photosensitive compound may thus be activated by light from the device.

Activation of a compound may change the compound in such a way that the compound or a reaction product of the activated compound may have therapeutic effect in vivo. For example, a compound may be activated by absorbing light to transition to an excited electronic state, such as an excited singlet or triplet state. A compound in an excited electronic state may then react to form physiologically active compounds. A compound in an excited electronic state may also directly or indirectly form reactive species such as radicals (including singlet oxygen radicals), radical ions, carbenes, or the like, which can readily react with materials in living cells or tissue.

For example, a photosensitive compound may be administered systemically by ingestion or injection, topically applying the compound to a specific treatment site on a patient's body, or by some other method. This may be followed by illumination of the treatment site with light having a wavelength or waveband corresponding to a characteristic absorption waveband of the photosensitive compound, such as at least about 500 nm or about 600 nm; and/or up to about 800 nm or about 1100 nm. Illumination in this manner may activate the photosensitive compound. Activating the photosensitive compound may cause singlet oxygen radicals and other reactive species to be generated, which may lead to a number of biological effects that may destroy the tissue which has absorbed the photosensitive compound such as abnormal or diseased tissue.

A photosensitive compound may be any compound, or a pharmaceutically acceptable salt, prodrug, or hydrate thereof, which may react as a direct or indirect result of absorption of ultraviolet, visible, or infrared light. In one embodiment, the photosensitive compound may react as a direct or indirect result of absorption of red light. The photosensitive compound may be a compound which is not naturally in the tissue. Alternatively, the photosensitive compound may naturally be present in the tissue, but an additional amount of the photosensitive compound may be administered to the mammal. In some embodiments, the photosensitive compound may selectively bind to one or more types of selected target cells and, when exposed to light of an appropriate waveband, may absorb the light, which may cause substances to be produced that impair or destroy the target cells.

While not limiting any embodiment, for some types of therapies, it may be helpful if the photosensitive compound has sufficiently low toxicity, or can be formulated to have sufficiently low toxicity, so as not to cause more harm than the disease or the condition that is to be treated with the phototherapy. In some embodiments, it may also be helpful if the photodegradation products of the photosensitive compounds are nontoxic.

Some non-limiting examples of photosensitive compounds or materials may be found in Kreimer-Bimbaum, *Sem. Hematol.*, 26:157-73 (1989), incorporated by reference herein in its entirety, and may include, but are not limited to, chlorins, e.g. tetrahydroxylphenyl chlorin (THPC) [652 nm] and N-aspartyl chlorin e6 [664 nm], phthalocyanines [600-700 nm], porphyrins, e.g. hematoporphyrin [HPD] [630 nm], purpurins, e.g. [1,2,4-trihydroxyanthraquinone] tin etiopurpurin [660 nm], methylene blue [668 nm, 609 nm], toluidine blue, texaphyrins, talaportin sodium (mono-L-aspartyl chlorine)[664 nm], and rostaporfin [664 nm].

A photosensitive agent can be administered in a dry formulation, such as a pill, a capsule, a suppository or a patch. The photosensitive agent may also be administered in a liquid formulation, either alone, with water, or with pharmaceutically acceptable excipients, such as those disclosed in Remington's Pharmaceutical Sciences. The liquid formulation also can be a suspension or an emulsion. Liposomal or lipophilic formulations may be desirable. If suspensions or emulsions are utilized, suitable excipients may include water, saline, dextrose, glycerol, and the like. These compositions may contain minor amounts of nontoxic auxiliary substances such as wetting or emulsifying agents, antioxidants, pH buffering agents, and the like. The above described formulations may be administered by methods which may include but are not limited to intradermal, intramuscular, intraperitoneal, intravenous, subcutaneous, intranasal, epidural, oral, sublingual, intranasal, intracerebral, intravaginal, transdermal, iontophoretical, rectally, by inhalation, or topically to the desired target area, for example, the body cavity (e.g., oral, nasal, rectal), ears, nose, eyes, or skin. The preferred mode of administration may be left to the discretion of the practitioner, and may depend in part upon the site of the medical condition (such as the site of cancer or viral infection).

The dose of photosensitive agent may vary. For example, the target tissue, cells, or composition, the optimal blood level, the animal's weight, and the timing and duration of the radiation administered, may affect the amount of photosensitive agent used. Depending on the photosensitive agent used, an equivalent optimal therapeutic level may be empirically established. The dose may be calculated to obtain a desired blood level of the photosensitive agent, which in some embodiments may be from about 0.001 g/mL or 0.01 µg/mL to about 100 µg/mL or about 1000 µg/mL.

The light may be administered by an external or an internal light source, such as a light-emitting device (e.g., an OLED) as described herein. The intensity or power density of radiation or light used to treat the target cell or target tissue may vary. In some embodiments, the intensity or power density may be in the range of about 0.1 mW/cm$^2$ to about 100 mW/cm$^2$, about 1 mW/cm$^2$ to about 50 mW/cm$^2$, about 3 mW/cm$^2$ to about 30 mW/cm$^2$, about 2 mW/cm$^2$ to about 20 mW/cm$^2$, about 3 mW/cm$^2$ to about 10 mW/cm$^2$, about 7 mW/cm$^2$ to about 10 mW/cm$^2$, about 3.5 mW/cm$^2$ to about 7 mW/cm$^2$, about 10 mW/cm$^2$, or any intensity in a range bounded by, or between, any of these values. The duration of radiation or light exposure administered to a subject may vary. In some embodiments, the exposure ranges from at least 1 second, at least about 1 minute, at least about 60 minutes, or at least about 2 hours; up to about 24 hours, up to about 48 hours, or up to about 72 hours; about 30 seconds; about 2 minutes to about 3 minutes; about 12 minutes; or, for any amount of time in a range bounded by, or between, any of these values.

A certain amount of light energy may be required to provide a therapeutic effect. This may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time. In some embodiments, the light dose or fluence provided to a wound may be about 0.01 $J/cm^2$ to about 50 $J/cm^2$, about 0.1 $J/cm^2$ to about 10 $J/cm^2$, about 0.05 $J/cm^2$ to about 15 $J/cm^2$, about 0.2 $J/cm^2$ to about 5 $J/cm^2$, about 0.2 $J/cm^2$, about 1 $J/cm^2$, about 5 $J/cm^2$, or any light dose in a range bounded by, or between, any of these values.

The intensity of light decreases with the square of the distance from the source of the light. For example, light 1 meter away from a source is four times as intense as light 2 meters from the same source. A dose of light and other properties related to intensity can similarly vary. Thus, unless otherwise stated, distance-dependent properties of light refer to the property at the location of the tissue being treated.

Figure 3:
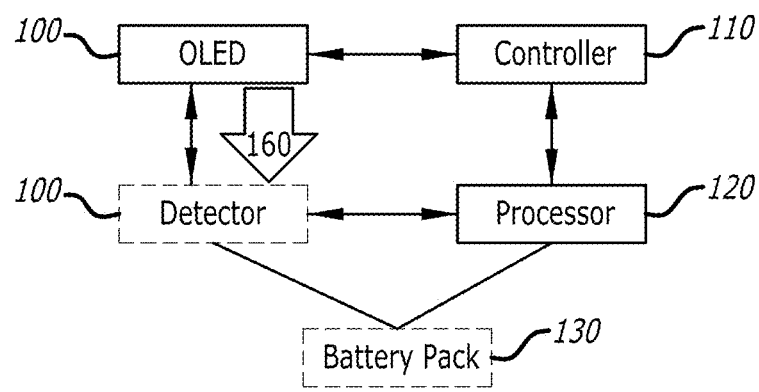
FIG. 3 is a schematic of some embodiments which further include a controller, a processor, and an optional detector.

FIG. 3 is a schematic of some embodiments which further include a controller 110 and processor 120 electrically connected to an OLED 100, which may help to provide a uniform power supply to facilitate homogeneous light exposure of the tissue. In some embodiments, the apparatus may further include an optional detector 140, such as photodiode, which may detect a portion of the light 160 emitted from the OLED 100, to help determine the amount of light being emitted by the OLED 100. For example, the detector 140 may communicate a signal related to the intensity of the light 160 received from the OLED 100 to the processor 120, which, based upon the signal received, may communicate any desired power output information to controller 110. Thus, these embodiments may provide real time feedback which allows the control of the intensity of light emitted from the OLED 100. The detector 140 and the processor 120 may be powered by compact power supply, such as a battery pack 130, or by some other power source.

In some embodiments related to phototherapy, an OLED device may further comprise a dosage component. A dosage component may be configured to control the device to provide a sufficient amount of light to achieve a therapeutic effect in a person or animal; e.g., a mammal. If a photosensitive compound is used, a dosage component may be configured to control the device to provide a sufficient amount of light to activate a sufficient portion of a photosensitive compound to provide a therapeutic effect for treating a disease in a mammal such as a human being.

For example, a dosage component may comprise a timer that is configured to control delivery of light from the device for an amount of time sufficient to deliver the appropriate light dosage. The timer may automatically stop the emission from the device once the appropriate light dosage has been delivered. The dosage component may also comprise a positioning component that positions the device so that emitted light is delivered to the appropriate area of a mammal body and is at an appropriate distance from the affected tissue to deliver an effective amount of light. The dosage component may be configured to work with a particular photosensitive compound, or may provide flexibility. For example, a physician, a veterinarian, or another appropriate medical practitioner may set the parameters of the dosage component for use by a patient outside of the practitioner's office, such as at the patient's home. In some embodiments, the device may be provided with a set of parameters for various photosensitive compounds to assist a medical practitioner in configuring the device.

For phototherapy, a device may comprise a light-emitting diode coupled to a flexible substrate. This may allow a device to be wrapped around a body part so as to provide uniform light to an entire surface of a body part.

In some embodiments, the device may further include a wireless transmitter electrically connected to a component of the apparatus generating treatment information; e.g., level of intensity, time of application, dosage amount, to communicate/transfer data to another external receiving device, such as a cell phone, personal data assistant, tablet, pager, or to a doctor's office. In some embodiments, the apparatus may further include an adhesive tape which may be used to attach the apparatus on the tissue surface so as to stabilize it on the target area.

For phototherapy and other applications, a wavelength convertor may be positioned in the device to receive at least a portion of light emitted from the organic light-emitting diode in a lower wavelength range, such as about 350 nm to less than about 600 nm, and convert at least a portion of the light received to light in a higher wavelength range, such as about 620 nm to about 640 nm. The wavelength convertor may be a powder, a film, a plate, or in some other form and, may comprise: yttrium aluminum garnet (YAG), alumina ($Al_2O_3$), yttria ($Y_2O_3$), titania ($TiO_2$), and the like. In some embodiments, the wavelength convertor may comprise at least one dopant which is an atom or an ion of an element such as Cr, Ce, Gd, La, Tb, Pr, Sm, Eu, etc.

In some embodiments, a wavelength convertor may comprise a translucent ceramic phosphor represented by a formula such as, but not limited to $(A_{1-x}E_x)_3D_5O_{12}$, $(Y_{1-x}E_x)_3D_5O_{12}$; $(Gd_{1-x}E_x)_3D_5O_{12}$; $(La_{1-x}E_x)_3D_5O_{12}$; $(Lu_{1-x}E_x)_3D_5O_{12}$; $(Tb_{1-x}E_x)_3D_5O_{12}$; $(A_{1-x}E_x)_3Al_5O_{12}$; $(A_{1-x}E_x)_3Ga_5O_{12}$; $(A_{1-x}E_x)_3In_5O_{12}$; $(A_{1-x}Ce_x)_3D_5O_{12}$; $(A_{1-x}Eu_x)_3D_5O_{12}$; $(A_{1-x}Tb_x)_3D_5O_{12}$; $(A_{1-x}E_x)_3Nd_5O_{12}$; and the like. In some embodiments, the ceramic may comprise a garnet, such as a YAG, with a dopant. Some embodiments provide a composition represented by the formula $(Y_{1-x}Ce_x)_3Al_5O_{12}$. In any of the above formulas, A may be Y, Gd, La, Lu, Tb, or a combination thereof; D may be Al, Ga, In, or a combination thereof; E may be Ce, Eu, Tb, Nd, or a combination thereof; and x may be in the range of about 0.0001 to about 0.1, from about 0.0001 to about 0.05, or alternatively, from about 0.01 to about 0.03.

Wound Healing

One example of a condition to which the phototherapy devices, systems and/or methods of the present disclosure can be applied is wound healing. Wound healing is impaired in some individuals, especially in those suffering from particular conditions such as diabetes. As the present disclosure demonstrates, phototherapy according to the embodiments described herein can assist in overall wound healing in individuals suffering from conditions that characterized by poor wound healing.

Wound healing is a sequential process and requires the activity of various cell types at the different stages of healing. The wound healing process generally comprises the inflammatory phase, in which is seen the early infiltration of polymorphonuclear neutrophils (PMNs) at the wound site, followed by infiltration of monocytes, which mature into macrophages, and the activation of macrophages. For example at least in humans, by day two after injury the macrophages become the predominant cell type at the wound site. This is followed by the proliferative phase, in which is seen angiogenesis or neovascularization, and fibroblast accumulation. For example at least in humans, fibroblasts are the predominant cell type at the wound site by the end of the first week. Also in the proliferative phase is granulation tissue growth, collagen deposition, and epithelialization.

Macrophages play an important role in wound healing. Other than wound debridement, macrophages are known to also secrete cytokines and growth factors to activate and recruit other cell types at the subsequent stages of wound healing, and depletion of macrophages results in a significant delay of wound healing. Insufficient classical macrophage activation has been shown in the early stage of wound healing in diabetic wounds (M. Miao et al., *Wound Repair Regen.* (2012), 20(2):203-13). However, prolonged inflammatory phase in diabetic wounds often causes delayed healing (MP Rodero et al., *Int. J. Clin. Exp. Pathol.* (2010), 3(7):643-53).

FGF2 has a number of effects during wound healing, including for example causing an increase in keratinocyte migration and proliferation, and recruitment of inflammatory cells. FGF2 also stimulates endothelial cell proliferation and neovascularization.

In some embodiments, light can be used in combination with wound dressings to effect accelerated wound healing. The wound dressing may include a hydrocolloid particles or material, for example as described in US 2008/0311178 (Jun Ishikura et al., filed Jun. 4, 2008); a transparent film, for example as described in U.S. Pat. No. 7,678,959 issued Mar. 16, 2010 to Okadam Katshiro et al.; and/or, an adhesive material. An adhesive may be any conventional adhesive and may have sufficient adhesion to keep the wound dressing or device in contact with a patient while not having too much adhesion such that wound dressing cannot be removed from the patient. In these methods, a wound dressing may be used alone or in combination with a photosensitive compound.

In some embodiments, at least a portion of a wound dressing is exposed to light from a device. The wound dressing may be applied to the wound of a mammal to effect accelerated healing. The dressing may be exposed to the light prior to and/or subsequent to application of the dressing to the wound site. Light in the red range may also be used in conjunction with light of other spectral wavelengths, for example blue or yellow, to facilitate post operative healing.

Figure 4:
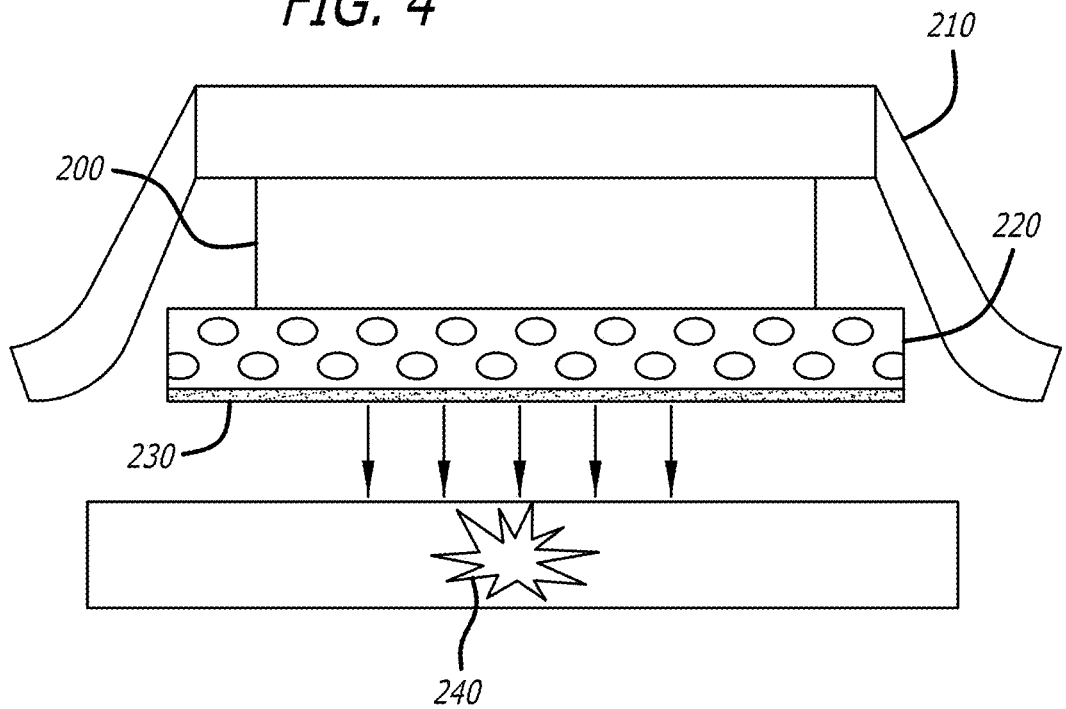
FIG. 4 depicts an embodiment of a wound dressing incorporating an OLED.

FIG. 4 illustrates a wound healing dressing that may incorporate a light-emitting device. OLED 200 may be disposed between flexible wrapping material 210 and hydrocolloid layer 220. There may be direct contact between OLED 200 and hydrocolloid layer 220, and in some embodiments, a surface of OLED 200 may be substantially covered by hydrocolloid layer 220. Adhesive layer 230 may be disposed between hydrocolloid layer 220 and wound 240. There may be direct contact between adhesive layer 230 and hydrocolloid layer 220, and in some embodiments, a surface of hydrocolloid layer 220 may be substantially covered by adhesive layer 230.

A flexible wrapping material, e.g. flexible wrapping material 210, may be any material that is suitable for wrapping a wound, such as gauze or medical tape.

A hydrocolloid layer, e.g. hydrocolloid layer 220, may include any hydrocolloid layer that may be suitable as a wound dressing and allows a therapeutic amount of light to pass through the dressing. Hydrocolloid layer 220 may be adhered to adhesive layer 230. In some embodiments, a hydrocolloid layer may be substantially transparent.

An adhesive layer, e.g. adhesive layer 230, may be any layer suitable for adhesion to a wound or skin surface that also allows a therapeutic amount of light to pass through the layer. In some embodiments, an adhesive layer may be substantially transparent.

Generally, it is helpful if the assembly of hydrocolloid layer and adhesive layer is capable of absorbing wound exudate and preventing or reducing the entry of bacteria or other pathogens into the wound.

Some commercial products that include a hydrocolloid layer and an adhesive layer include YU-KI BAN® brand dressing (Nitto Denko [Medical Related Products Div., Tokyo, Japan), AMPARO® brand dressing (Amparo Medical Technologies, Inc., Placentia, Calif., USA), VIGILON® brand dressing (Bard Medical Division [C. R. Bard] Covington, Ga., USA), COMFEEL® brand dressing (Coloplast US, Minneapolis, Minn., USA), AND ABSOCURE-SURGICAL® brand dressing (Nitto Denko, Medical Related Products Div., Tokyo, Japan).

Incorporation of a hydrocolloid layer between the OLED and the wound may enhance the emission of light from the OLED by about 1.1 times to about 2 times, or about 1.2 times to about 1.5 times, as compared to application of light from the OLED without the hydrocolloid layer between the OLED and the wound.

The light may be administered by an external or an internal light source, such as a light-emitting device (e.g., an OLED) as described herein. The intensity or power density of radiation or light used to treat the target cell or target tissue may vary. In some embodiments, the intensity or power density may be in the range of about 0.1 mW/cm$^2$ to about 100 mW/cm$^2$, about 1 mW/cm$^2$ to about 50 mW/cm$^2$, about 3 mW/cm$^2$ to about 30 mW/cm$^2$, about 3.5 mW/cm$^2$ to about 15 mW/cm$^2$, about 2 mW/cm$^2$ to about 20 mW/cm$^2$, about 3 mW/cm$^2$ to about 10 mW/cm$^2$, about 7 mW/cm$^2$ to about 10 mW/cm$^2$, about 3.5 mW/cm$^2$ to about 7 mW/cm$^2$, about 10 mW/cm$^2$, or any intensity in a range bounded by, or between, any of these values. The duration of radiation or light exposure administered to a subject may vary. In some embodiments, the exposure ranges from at least 1 second, at least about 1 minute, at least about 60 minutes, or at least about 2 hours; up to about 24 hours, up to about 48 hours, or up to about 72 hours; about 30 seconds; about 2 minutes to about 3 minutes; about 12 minutes; or, for any amount of time in a range bounded by, or between, any of these values.

A certain amount of light energy may be required to provide a therapeutic effect. This may be accomplished by using a higher power light source, which may provide the needed energy in a shorter period of time, or a lower power light source may be used for a longer period of time. Thus, a longer exposure to the light may allow a lower power light source to be used, while a higher power light source may allow the treatment to be done in a shorter time. In some embodiments, the light dose or fluence provided to a wound may be about 0.01 J/cm$^2$ to about 50 J/cm$^2$, about 0.1 J/cm$^2$ to about 10 J/cm$^2$, about 0.05 J/cm$^2$ to about 15 J/cm$^2$, about 0.2 J/cm$^2$ to about 5 J/cm$^2$, about 1 J/cm$^2$ to about 5 J/cm$^2$, about 0.2 J/cm$^2$, about 1 J/cm$^2$, about 5 J/cm$^2$, or any light dose in a range bounded by, or between, any of these values.

Since wound healing interacts the surface tissue first, penetration depth can be smaller than other forms of phototherapy involving tissue further below the surface. Light with appropriate wavelength in the range of 470 nm to 700 nm, or 600 nm to 700 nm, such as 515 nm, 565 nm, 600 nm, 630 nm, or 650 nm may be effective for wound healing. Light interacts with the superficial tissue and enhance growth factors such as fibroblast, keratinocytes, lymphocytes and may heal wounds through inflammation, proliferation and maturation.

The Examples of the present disclosure demonstrate that the OLED devices as described herein are useful in overall wound healing, and they also demonstrate the positive effects of phototherapy, and in particular OLED-device phototherapy, on the individual processes involved in wound healing.

Figure 24A:
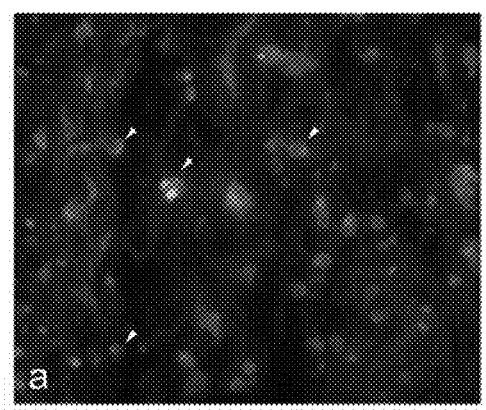
FIGS. 24A-24C show the anti-CD68 antibody ED1 immunohistochemistry of macrophages in control (FIG. 24A) and OLED-treated (FIG. 24B) groups.
Figure 24B:
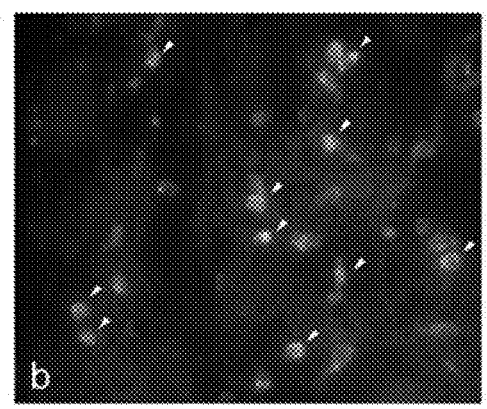

As one example, significantly more intense macrophage labeling was demonstrated in OLED-treated wounds (see FIG. 24B) than in untreated controls (see FIG. 24A). Quantification of these images indicated that a statistically higher macrophage response was seen in the OLED-treated group than in untreated controls, thus indicating that OLED treatment positively affects macrophage activation in diabetic wounds, where there is otherwise insufficient macrophage activation in the early stages of wound healing, and in so doing, promotes wound healing.

As another example, rats with OLED-treated wounds in the Examples herein had a significantly higher level of FGF2 expression than the untreated controls. This result is comparable with previous studies (see, e.g., Byrnes K R et al., *Photomed Laser Surg.* (2004), 22(4):281-90) using the Fat Sand Rat, in which laser irradiation (632 nm wavelength) promoted FGF2 expression in the diabetic wound.

Surprisingly, the results in the Examples of the present disclosure demonstrate that different phototherapy methods, such as OLED vs. laser, promote different aspects of wound healing. For example, OLED-specific treatment promoted vascularity in the wound healing process to a greater extent than did laser phototherapy. See FIG. 22E.

OLED devices can be used assist in wound healing in persons suffering from conditions characterized by delayed or problematic wound healing. Some of the conditions that give rise to or manifest delayed or problematic wound healing include, for example but without limitation, metabolic diseases, immunosuppression, connective tissue disorders, and so forth. Some examples of such metabolic diseases include, without limitation, acute intermittent porphyria, alcaptonuria, carbamoyl phosphate synthetase I deficiency, diabetes, glutaric acidemia type 1, congenital adrenal hyperplasia, Gaucher's disease, glycogen storage disease, Kearns-Sayre syndrome, Lesch-Nyhan syndrome, lipoid congenital adrenal hyperplasia, maple syrup urine disease, medium-chain acyl-coenzyme A dehydrogenase deficiency (or MCADD), Niemann Pick disease, phenylketonuria, and Zellweger syndrome. Other embodiments relate to the use of OLED devices for wound healing in patients suffering from conditions specifically related to disorders of vascularization, such as for example peripheral vascular disease, diabetes type I or II, and some cancers.

In some embodiments the OLED devices can be used throughout the process of wound healing, without regard to the particular phase of wound healing or particular time points. In other embodiments, the use of an OLED devices for wound therapy can be targeted to the specific time points in wound healing where OLED therapy can be most effective and/or most beneficial. This targeted use of OLED therapy can be desirable for several reasons, including but not limited to reducing the cost of therapy or supplies, reducing the over all time of therapy, reducing discomfort to the patient, etc. As one example, because OLED therapy is especially effective at activating vascularity (see, e.g., 22E), certain embodiments of the present disclosure relate to the use of OLED devices during the stage of wound healing when vascularization is known to be at its height, such as from a few days after injury, e.g. about 2, 3, or 4 days, to the end of the first week after injury, e.g. about 6, 7, or 8 days.

LISTED EMBODIMENTS

Embodiment 1

A light-emitting device for use in phototherapy comprising:
a light-emitting layer comprising a luminescent compound that has a peak emission of about 620 nm to about 640 nm;
wherein the device is configured to provide an amount of light from the light-emitting layer effective to treat a wound of a mammal.

Embodiment 2

The device of claim 1, wherein the device is configured provide light to the wound at a power density of about 2 mW/cm$^2$ to about 20 mW/cm$^2$.

Embodiment 3

The device of embodiment 1, wherein the device is configured provide light to the wound at a power density of about 7 mW/cm$^2$ to about 10 mW/cm$^2$.

Embodiment 4

The device of embodiment 1 or 2, wherein the device further comprises a dosage component configured to deliver a light dose of about 0.1 J/cm$^2$ to about 10 J/cm$^2$ to a wound of a human being.

Embodiment 5

The device of embodiment 3, wherein the dosage component comprises a timer coupled to a positioning component.

Embodiment 6

The device of any one of the preceding embodiments, wherein the device comprises a flexible substrate comprising an organic light-emitting diode coupled to the flexible substrate, wherein the light emitting diode comprises the light-emitting layer disposed between an anode and a cathode.

Embodiment 7

The device of any one of the preceding embodiments, further comprising a capping layer disposed on a cathode.

Embodiment 8

A phototherapy system comprising:
a device according to any one of embodiments 1-7; and
a wound dressing.

23

Embodiment 9

The phototherapy system of embodiment 8, further comprising a dosage component configured to deliver a light dose of about 0.05 J/cm² to about 15 J/cm² to a wound of a human being.

Embodiment 10

The phototherapy system of embodiment 8, wherein the dosage component is configured to deliver a light dose of about 0.2 J/cm² to about 5 J/cm² to the wound of the human being.

Embodiment 11

The phototherapy system of any one of embodiments 8-10, further comprising a hydrocolloid layer that is in direct contact with the device, wherein the phototherapy system is configured so that the hydrocolloid layer is disposed between the device and a wound when the phototherapy system is used to treat the wound.

Embodiment 12

The phototherapy system of embodiment 11, further comprising an adhesive layer, wherein the phototherapy system is configured so that the adhesive layer is disposed between, and in contact with the, wound and the hydrocolloid layer when the phototherapy system is used to treat the wound.

Embodiment 13

The phototherapy system of embodiment 12, wherein the hydrocolloid layer enhances the efficiency of light emission from the device.

Embodiment 14

A method of treating a wound comprising: exposing at least a portion of a wound to light from a device or system of any one of embodiments 1-13.

Embodiment 15

The method of embodiment 14, wherein the wound is of a human being with diabetes.

Embodiment 16

The method of embodiment 14 or 15, wherein a light dose of 1 J/cm² to 5 J/cm² is delivered to the wound.

Embodiment 17

The method of embodiment 16, wherein a light dose of 5 J/cm² is delivered to the wound.

Embodiment 18

The method of any one of embodiments 14-18, wherein the wound is treated from 2 days to 8 days after an injury.

24

EXAMPLES

Example 1: Synthetic Examples

The following are examples of some methods that may be used to prepare compounds described herein.

Example 1.1

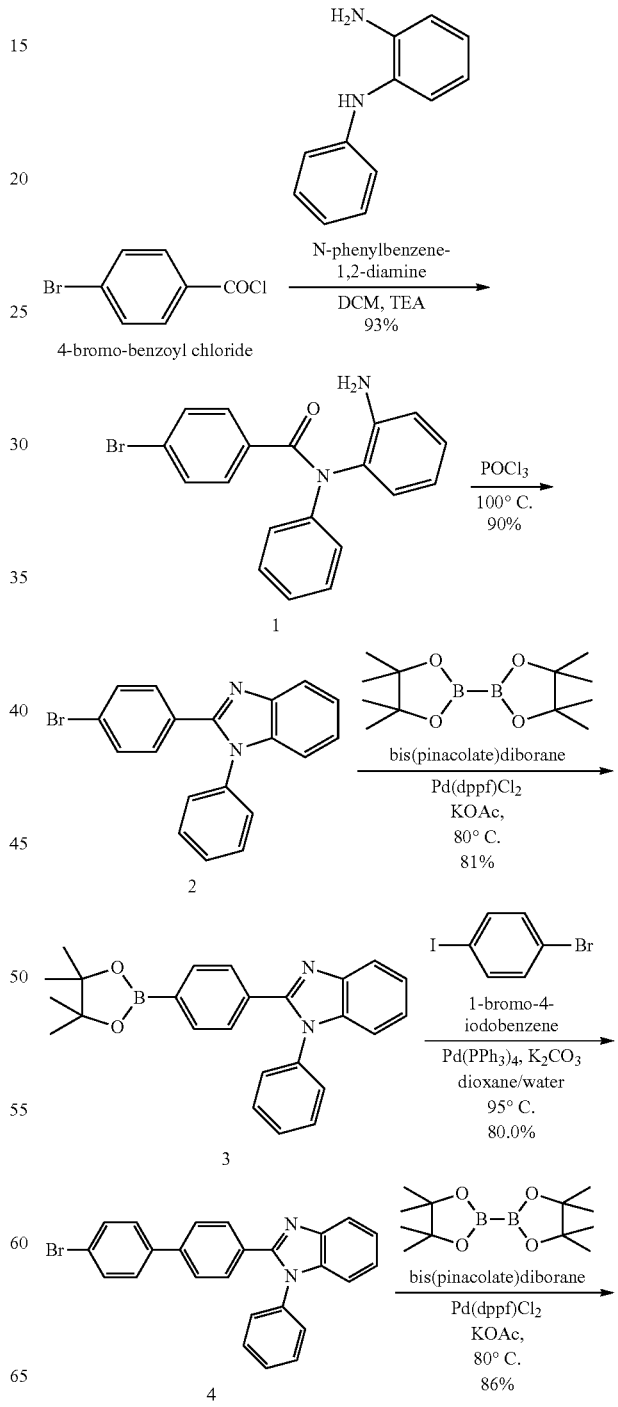

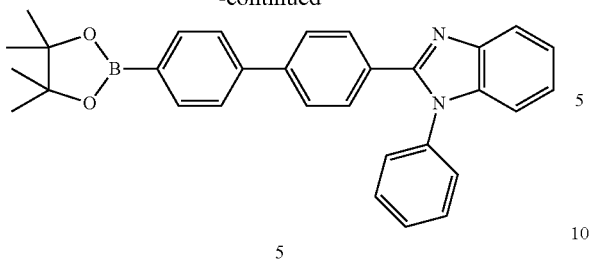

5

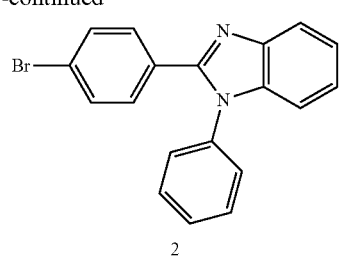

2

Example 1.1.1

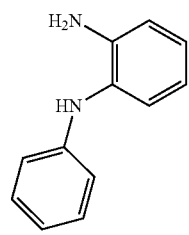

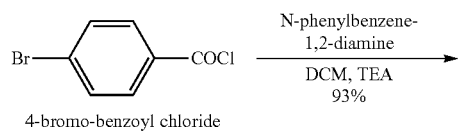

4-bromo-benzoyl chloride

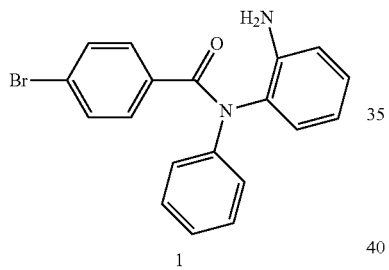

1

4-Bromo-N-(2-(phenylamino)phenyl)benzamide (1): To a solution of 4-bromo-benzoyl chloride (11 g, 50 mmol) in anhydrous dichloromethane (DCM) (100 mL), was added N-phenylbenzene-1,2-diamine (10.2 g, 55 mmol), then triethylamine (TEA) (17 mL, 122 mmol) slowly. The whole was stirred at room temperature (RT) overnight. Filtration gave a white solid 1 (6.5 g). The filtrate was worked up with water (300 mL), then extracted with DCM (300 mL) three times. The organic phase was collected and dried over MgSO$_4$, concentrated and recrystallized in DCM/hexanes to give another portion of white solid 1 (10.6 g). Total amount of product 1 is 17.1 g, in 93% yield.

Example 1.1.2

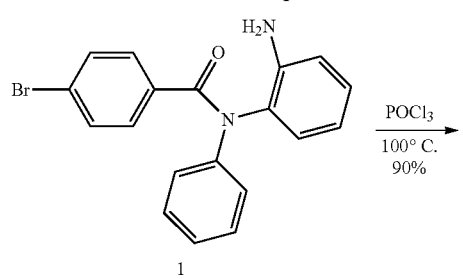

1

2-(4-bromophenyl)-1-phenyl-1H-benzo[d]imidazole (2): To a suspension of amide 1 (9.6 g, 26 mmol) in anhydrous 1,4-dioxane (100 mL) was added phosphorus oxychloride (POCl$_3$) (9.2 mL, 100 mmol) slowly. The whole was then heated at 100° C. overnight. After cooling to room temperature (RT), the mixture was poured into ice (200 g) with stirring. Filtration, followed by recrystallization in DCM/hexanes gave a pale grey solid 2 (8.2 g, in 90% yield).

Example 1.1.3

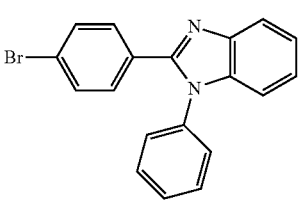

2

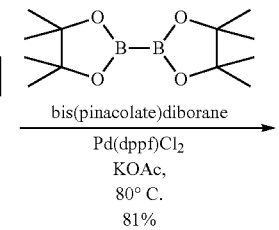

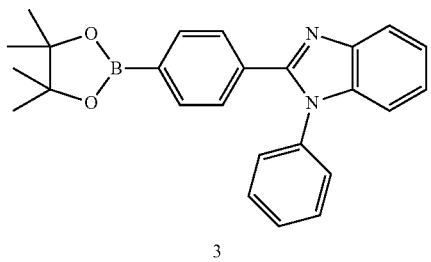

3

1-phenyl-2-(4-(4,4,5,5-tetramethyl-1,3,2-dioxaborolan-2-yl)phenyl)-1H-benzo[d]imidazole (3): A mixture of Compound 2 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 mL) was heated at 80° C. under argon overnight. After cooling to RT, the whole was diluted with ethyl acetate (80 mL) then filtered. The solution was absorbed on silica gel, then purified by column chromatography (hexanes/ethyl acetate 5:1 to 3:1) to give a white solid 3 (0.64 g, in 81% yield).

Example 1.1.3

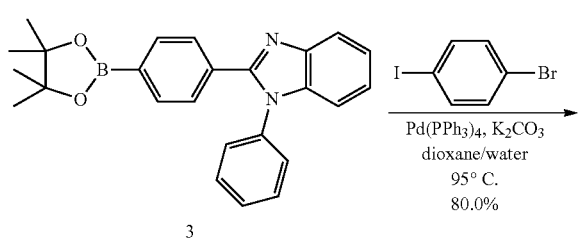

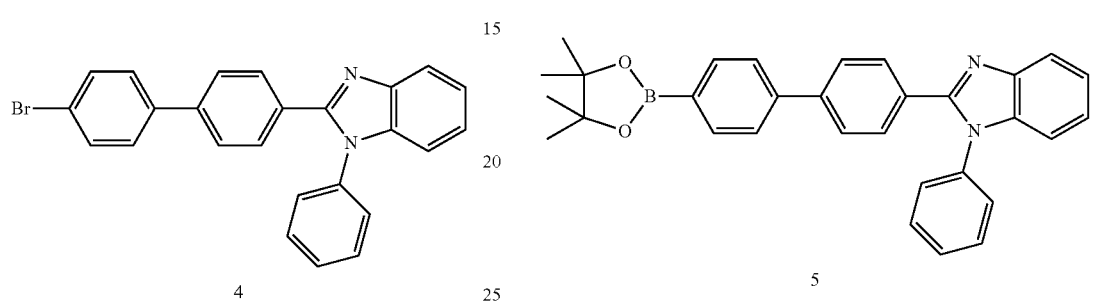

2-(4'-bromo-[1,1'-biphenyl]-4-yl)-1-phenyl-1H-benzo[d]imidazole (4): A mixture of compound 3 (4.01 g, 10.1 mmol), 1-bromo-4-iodobenzene (5.73 g, 20.2 mmol), Pd(PPh$_3$)$_4$ (0.58 g, 0.5 mmol) and potassium carbonate (4.2 g, 30 mmol) in dioxane/water (60 mL/10 mL) was degassed and heated at 95° C. overnight. After being cooled to RT, the mixture was poured into ethyl acetate (250 mL), washed with brine, dried over Na$_2$SO$_4$, then loaded on silica gel, purified by flash column (hexanes to hexanes/ethyl acetate 4:1) to give a light yellow solid washed with methanol and dried in air (3.39 g, in 80% yield).

Example 1.1.4

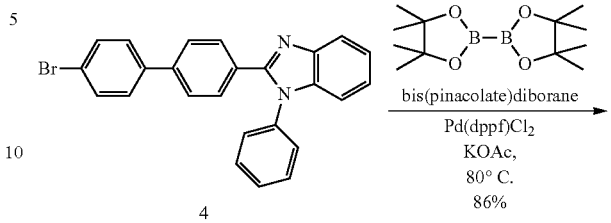

1-phenyl-2-(4'-(4,4,5,5-tetramethyl-1,3,2-dioxaborolan-2-yl)-[1,1'-biphenyl]-4-yl)-1H-benzo[d]imidazole (5): A mixture of Compound 4 (1.2 g, 2.82 mmol), bis(pinacolate)diborane (0.72 g, 2.82 mmol), bis(diphenylphosphino)ferrocene]dichloropalladium (Pd(dppf)Cl$_2$) (0.10 g, 0.14 mmol) and anhydrous potassium acetate (KOAc) (2.0 g, 20 mmol) in 1,4-dioxane (45 mL) was heated at 80° C. under argon overnight. After cooling to RT, the whole was diluted with ethyl acetate (150 mL) then filtered. The solution was absorbed on silica gel, then purified by column chromatography (hexanes/ethyl acetate 5:1 to 3:1) to give a white solid 5 (1.14 g, in 86% yield).

Example 1.2

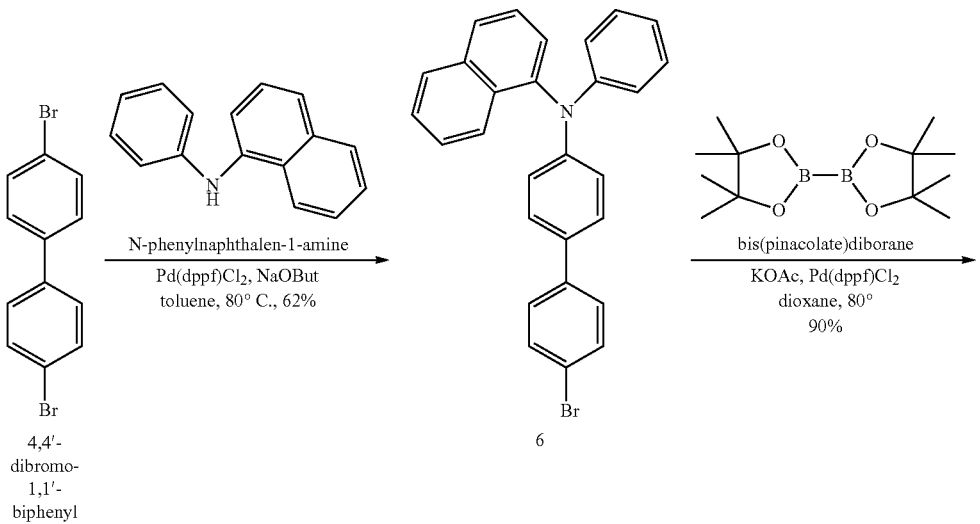

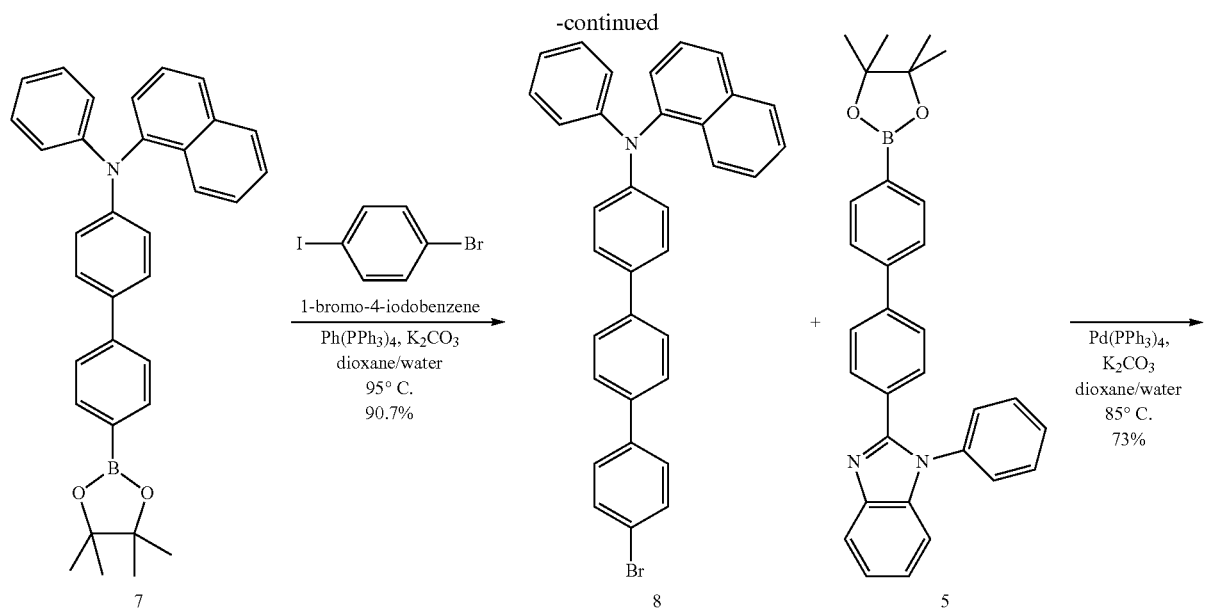
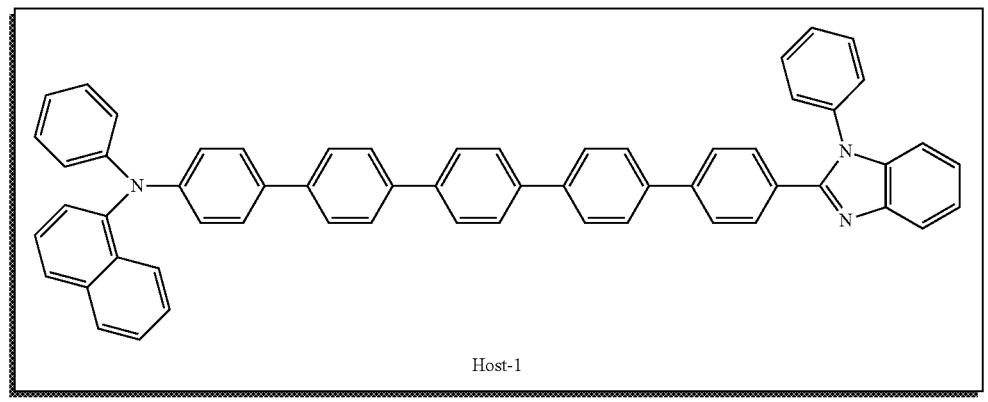
Example 1.2.1
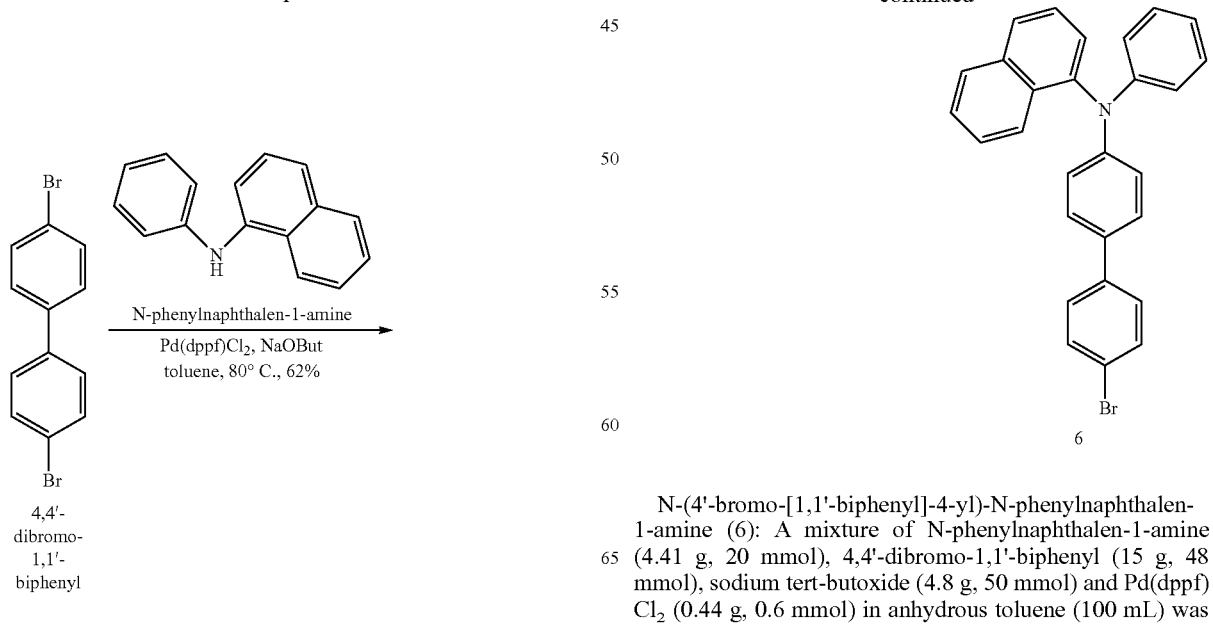
N-(4'-bromo-[1,1'-biphenyl]-4-yl)-N-phenylnaphthalen-1-amine (6): A mixture of N-phenylnaphthalen-1-amine (4.41 g, 20 mmol), 4,4'-dibromo-1,1'-biphenyl (15 g, 48 mmol), sodium tert-butoxide (4.8 g, 50 mmol) and Pd(dppf)Cl$_2$ (0.44 g, 0.6 mmol) in anhydrous toluene (100 mL) was degassed and heated at 80° C. for 10 hours. After cooling to RT, the mixture was poured into dichloromethane (400 mL) and stirred for 30 min, then washed with brine (100 mL). The organic is collected and dried over Na₂SO₄, loaded on silica gel, and purified by flash column (hexanes to hexanes/ethyl acetate 90:1) to give a solid which was washed with methanol and dried under air to give a white solid 4 (5.58 g, in 62% yield).

Example 1.2.2

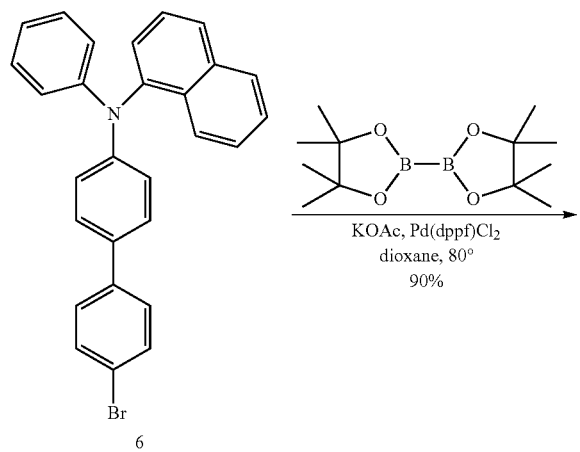

Example 1.2.3

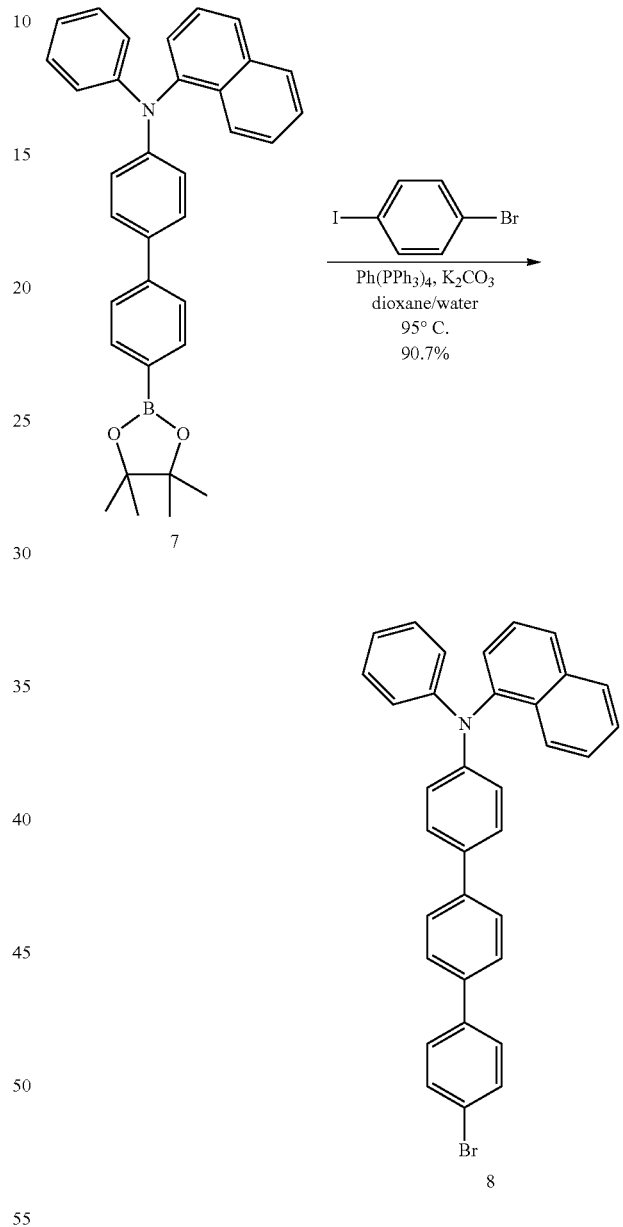

N-phenyl-N-(4'-(4,4,5,5-tetramethyl-1,3,2-dioxaborolan-2-yl)-[1,1'-biphenyl]-4-yl)naphthalen-1-amine (7): A mixture of Compound 6 (5.5 g, 12.2 mmol), bis(pinacolate) diborane (3.10 g, 12.2 mmol), Pd(dppf)Cl₂ (0.446 mg, 0.6 mmol) and KOAc (5.5 g, 56 mmol) in anhydrous dioxane (60 mL) was degassed and heated at 80° C. overnight. After being cooled to RT, the mixture was poured into ethyl acetate (200 mL), and washed with brine (150 mL). The organic solution was dried over Na₂SO₄, loaded on silica gel and purified by flash column (hexanes to hexanes/ethyl acetate 30:1) to collect the major fraction. After removal of solvent, the solid was washed with methanol, filtered and dried in air to give a white solid 7 (5.50 g, in 90% yield).

N-(4"-bromo-[1,1':4',1"-terphenyl]-4-yl)-N-phenylnaphthalen-1-amine (8): A mixture of compound 7 (4.5 g, 9.0 mmol), 1-bromo-4-iodobenzene (5.12 g, 18 mmol), Pd(PPh₃)₄ (0.52 g, 0.45 mmol) and potassium carbonate (4.436 g, 32 mmol) in dioxane/water (150 mL/30 mL) was degassed and heated at 95° C. overnight. After being cooled to RT, the mixture was poured into dichloromethane (300 mL), washed with brine, dried over Na₂SO₄, then loaded on silica gel, purified by flash column (hexanes to hexanes/ethyl acetate 20:1) to give a light yellow solid 8 (4.30 g, in 90.7% yield).

Example 1.2.4

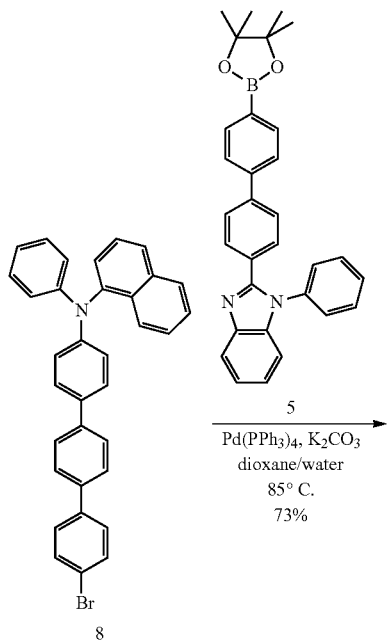

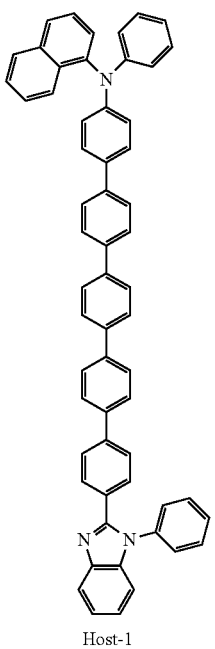

Host-1

Host-1: A mixture of compound 8 (1.50 g, 2.47 mmol), compound 5 (1.11 g, 2.35 mmol), Pd(PPh$_3$)$_4$ (0.16 g, 0.14 mmol) and potassium carbonate (1.38 g, 10 mmol) in dioxane/water (60 mL/10 mL) was degassed and heated at 85° C. for 18 hours. After being cooled to RT, the mixture was filtered. The solid and the filtrate were collected separately. The solid from the first filtration was redissolved in dichloromethane (100 mL), loaded on silica gel, and purified by flash column (dichloromethane to dichloromethane/ethyl acetate 9:1) to collect the desired fraction, concentrated. The white precipitate was filtered and dried in air to give a light yellow solid, Host-1 (1.35 g). The overall yield is 73%. LCMS data: calculated for C$_{59}$H$_{42}$N$_3$ (M+H): 792.3; found m/e=792.

Example 2: OLED Device Configuration and Performance

A device configured as shown in FIG. 1 can be prepared as described below. Such a device comprises the following layers in the order given: an ITO anode 5, a PEDOT hole-injection layer 10, an NPB hole-transport layer 15, a light-emitting layer 20, a TPBI electron-transport and hole-blocking layer 30, and a LiF/Al cathode 35.

For these particular examples, the ITO anode 5 was about 150 nm thick; the PEDOT hole injection layer 10 was about 30 nm thick; the NPB hole-transport layer 15 was about 40 nm thick; the light-emitting layer 20 was about 30 nm thick; the TPBI electron transport and hole blocking layer 30 was about 30 nm thick; the LiF sublayer (not shown) of the cathode 35 was about 0.5 nm thick; and the Al sublayer of the cathode (not shown) was about 120 nm thick. The device was then encapsulated with a getter attached glass cap to cover the emissive area of the OLED device in order to protect from moisture, oxidation or mechanical damage. Each individual device had an area of about 12 mm$^2$.

Fabrication of Light-Emitting Devices:

Device A

ITO substrates having sheet resistance of about 14 ohm/sq were cleaned ultrasonically and sequentially in detergent, water, acetone and then IPA; and then dried in an oven at 80° C. for about 30 min under ambient environment. Substrates were then baked at about 200° C. for about 1 hour in an ambient environment, then under UV-ozone treatment for about 30 minutes. PEDOT:PSS (hole-injection material) was then spin-coated on the annealed substrate at about 4000 rpm for about 30 sec. The coated layer was then baked at about 100° C. for 30 min in an ambient environment, followed by baking at 200° C. for 30 min inside a glove box (N$_2$ environment). The substrate was then transferred into a vacuum chamber, where 4,4'-bis[N-(naphthyl)-N-phenyl-amino]biphenyl (NPB) [hole transporting material] was vacuum deposited at a rate of about 0.1 nm/s rate under a base pressure of about 2×10$^{-7}$ torr. Bis(1-phenylisoquinoline)(acetylacetonate)iridium (III) ("Ir(piq)$_2$acac") (10 wt %) was co-deposited as an emissive layer with Host-1 material at about 0.01 nm/s and about 0.10 nm/s, respectively, to make the appropriate thickness ratio. 1,3,5-Tris(1-phenyl-1H-benzimidazol-)2-yl)benzene (TPBI) was then deposited at about 0.1 nm/s rate on the emissive layer. A layer of lithium fluoride (LiF) (electron injection material) was deposited at about 0.005 nm/s rate followed by deposition of the cathode as Aluminum (Al) at about 0.3 nm/s rate.

Figure 5:
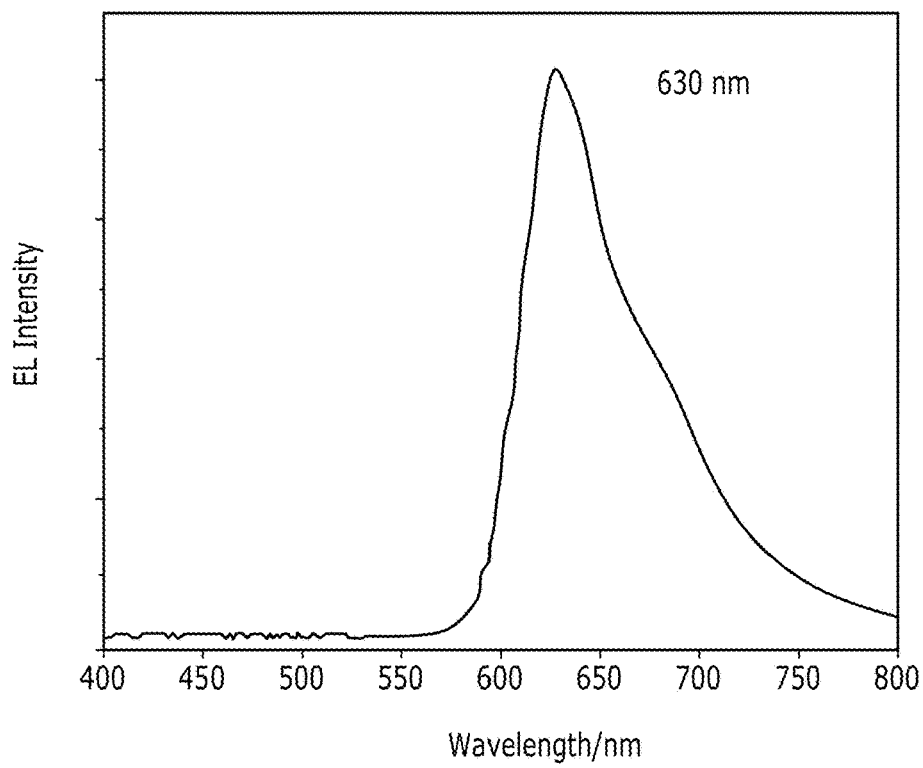
FIG. 5 shows the electroluminescence (EL) spectrum of the embodiment of Device A.
Figure 6:
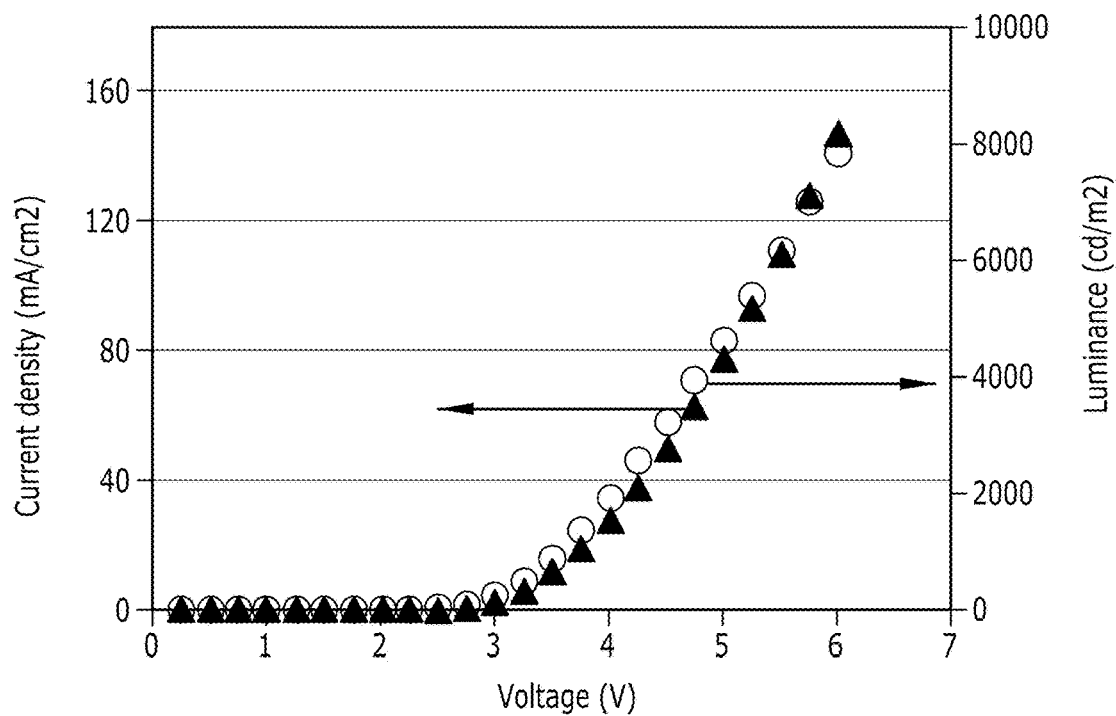
FIG. 6 is a plot of the current density and luminance (brightness) as a function of voltage of Device A.

EL spectra, shown in FIG. 5, was measured with a Spectrascan spectroradiometer PR-670 (Photo Research, Inc., Chatsworth, Calif., USA); and I-V-L characteristics were taken with a Keithley 2612 SourceMeter (Keithley Instruments, Inc., Cleveland, Ohio, USA) and PR-670. In addition, device performance of the Device A was evaluated by measuring the current density (mA/cm$^2$, diamonds) and luminance (cd/m$^2$, open circles) as a function of the driving voltage, as shown in FIG. 6.

Figure 7:
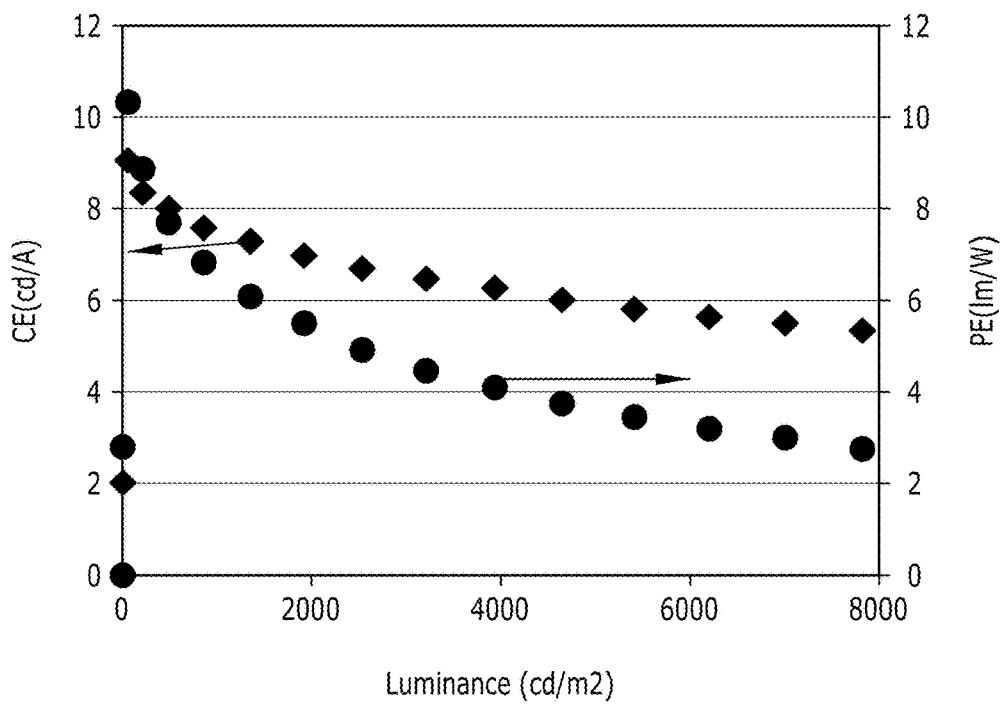
FIG. 7 is a plot of current efficiency and power efficiency as a function of luminance of Device A.

FIG. 7 is a plot of current efficiency (cd/A, diamonds) and power efficiency (lm/W, filled circles) as a function of luminance (cd/m$^2$) for the Device A. The turn-on voltage for the device was about 2.5 volts and the maximum luminance was about 39,700 cd/m$^2$ with 12 mm$^2$ area device at about 8V. The EQE (external quantum efficiency), luminous efficiency and power efficiency of the device at 1000 cd/m$^2$ were about 15.5%, 12.3 cd/A and 10.4 lm/w at 630 nm emission.

Device B

Device B was fabricated in a manner similar to the following. The substrate (glass-SiON/Metal foil) was cleaned ultrasonically and sequentially in detergent, water, acetone and then IPA; and then dried in an oven at about 80° C. for about 30 min under ambient environment. Substrate was then baked at about 200° C. for about 1 hour under ambient environment, then under UV-ozone treatment for about 30 minutes. Soon after UV-ozone treatment, substrates were loaded into a deposition chamber. A bi-layer reflective type bottom anode, e.g., Al (about 50 nm) and Ag (about 40 nm) were deposited sequentially at a rate of about 0.1 nm/s. A hole injection layer as dipyrazino[2,3-f:2',3'-h]quinoxaline-2,3,6,7,10,11-hexacarbonitrile (HAT-CN, about 10 nm) was deposited as on reflective anode. NPB (about 40 nm) was then deposited as a hole-transport layer. Bis(1-phenylisoquinoline)(acetylacetonate)iridium (III) ("Ir(piq)$_2$acac") (10 wt %) was co-deposited as an emissive layer with Host-8 material at about 0.01 nm/s and about 0.10 nm/s, respectively, to make the appropriate thickness ratio and a total thickness of about 20 nm. 1,3,5-Tris(1-phenyl-1H-benzimidazol-)2-yl)benzene (TPBI, about 50 nm) was then deposited at about 0.1 nm/s rate on the emissive layer. A thin layer of lithium fluoride (LiF, about 1 nm) (electron-injecting material) was deposited at about 0.005 nm/s rate, followed by deposition of the magnesium (Mg, about 1 nm) at about 0.005 nm/s rate. A semi-transparent cathode (about 16 nm) was deposited by co-deposition of magnesium (Mg) and silver (Ag) at a ratio of about 1:3 by weight. Finally a capping layer as NPB (about 60 nm) was deposited to enhance light output by micro cavity effect. All the deposition was done at a base pressure of about 2×10$^{-7}$ torr.

Referring to FIG. 2, the first anode sublayer 7 was Al (about 50 nm thick), the second anode sublayer 9 was Ag (about 40 nm thick), the hole-injecting layer 10 was HAT-CN (about 10 nm thick), the hole-transport layer 15 was NPB (about 40 nm thick), the light-emitting layer 20 was Host-8: Ir(piq)$_2$acac (about 20 nm thick), the electron-transport layer 30 was TPBI (about 50 nm thick), the electron-injecting layer 25 was LiF (about 1 nm thick), the second cathode sublayer was Mg (about 1 nm thick), the first cathode sublayer was Mg:Ag (about 16 nm thick), and the capping layer 40 was NPB (about 60 nm thick). The device was then encapsulated with a getter attached clear glass cap to cover the emissive area of the OLED device in order to protect from moisture, oxidation or mechanical damage. In order to minimize heat effect for such large area device, a heat dissipation layer 1 can be attached on the backside of the substrate 3 with a heat sink. This layer was a typical Al heat sink with fin structure. Other materials such as Cu-film and alloy films can also be used for a similar purpose depending on the thermal conductivity of the materials. Each individual device has an area of about 1.8 cm$^2$.

Figure 8:
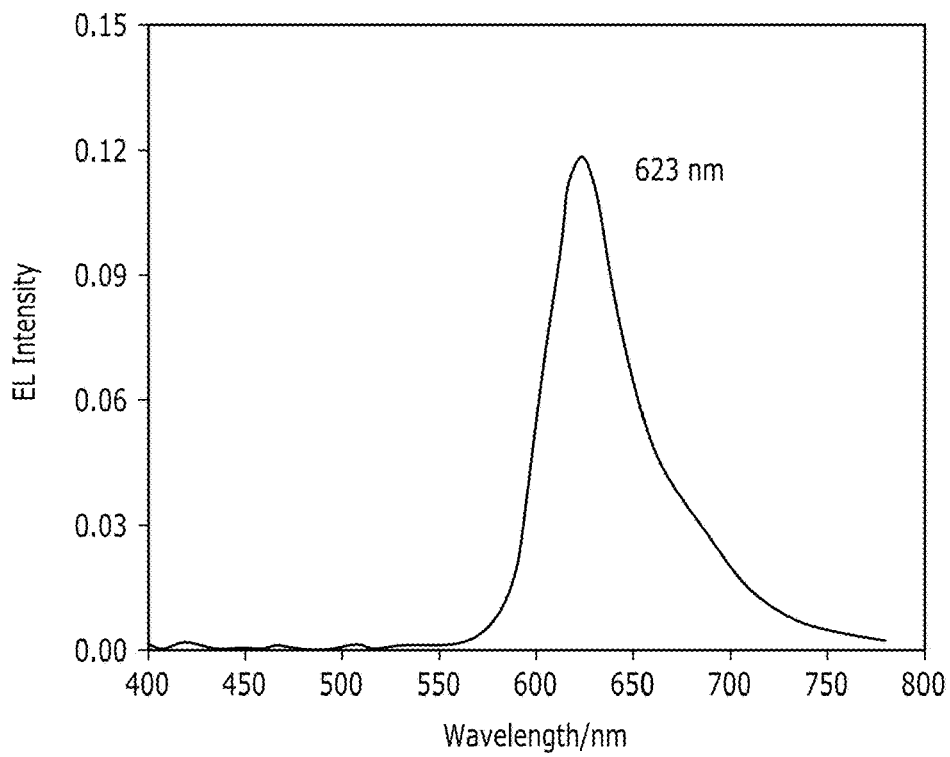
FIG. 8 shows the EL spectrum of Device B.

Performance of the Device B was evaluated. The EL spectrum of the device, shown in FIG. 8 (EL intensity as a function of wavelength in nm) was measured with a Spectrascan spectroradiometer PR-670 (Photo Research, Inc., Chatsworth, Calif., USA). The peak in intensity shown in FIG. 8 is at 623 nm. I-V-L characteristics were taken with a Hamamatsu integrated sphere system (Hamamatsu Photonics K. K., Hamamatsu City, Japan, Model C9920-11 [brightness light distribution characteristics measurement system] and A-10119 [optical box for brightness measurements]). In addition, device performance was evaluated by measuring the luminance and current density as a function of the driving voltage.

Figure 9:
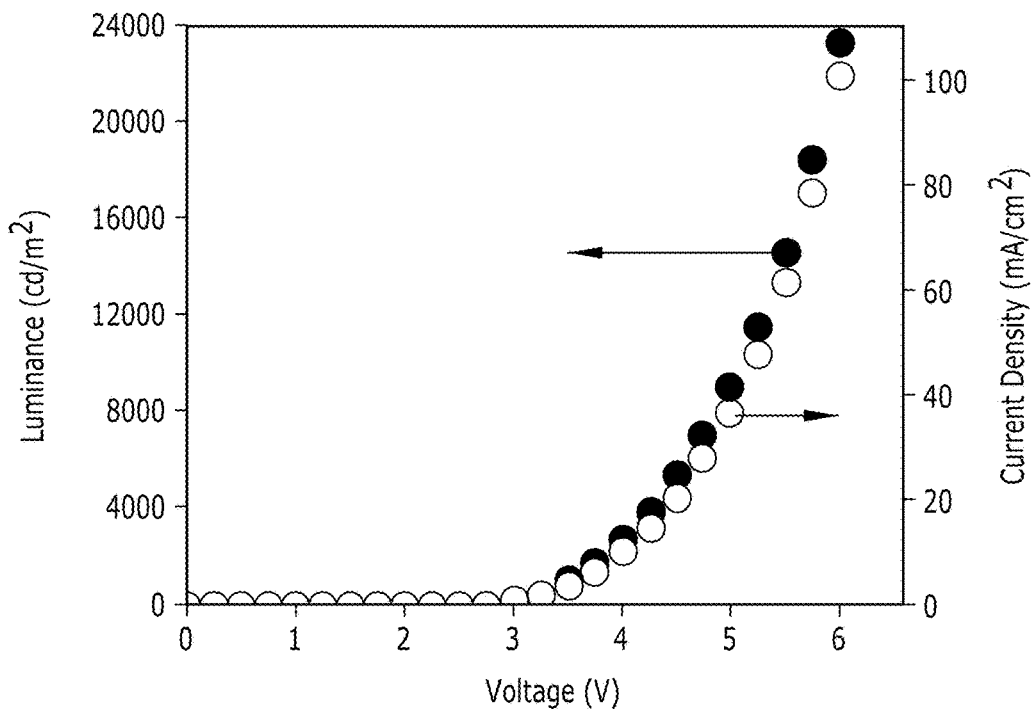
FIG. 9 is a plot of luminance and current density as a function of voltage of Device B.

FIG. 9 is a plot of luminance in cd/m$^2$ (filled circles) and current density in mA/cm$^2$ (open circles) as a function of applied voltage (V). The plot shows that the light power output of the device is sufficient for phototherapy at a voltage range that may be used for that application.

Figure 10:
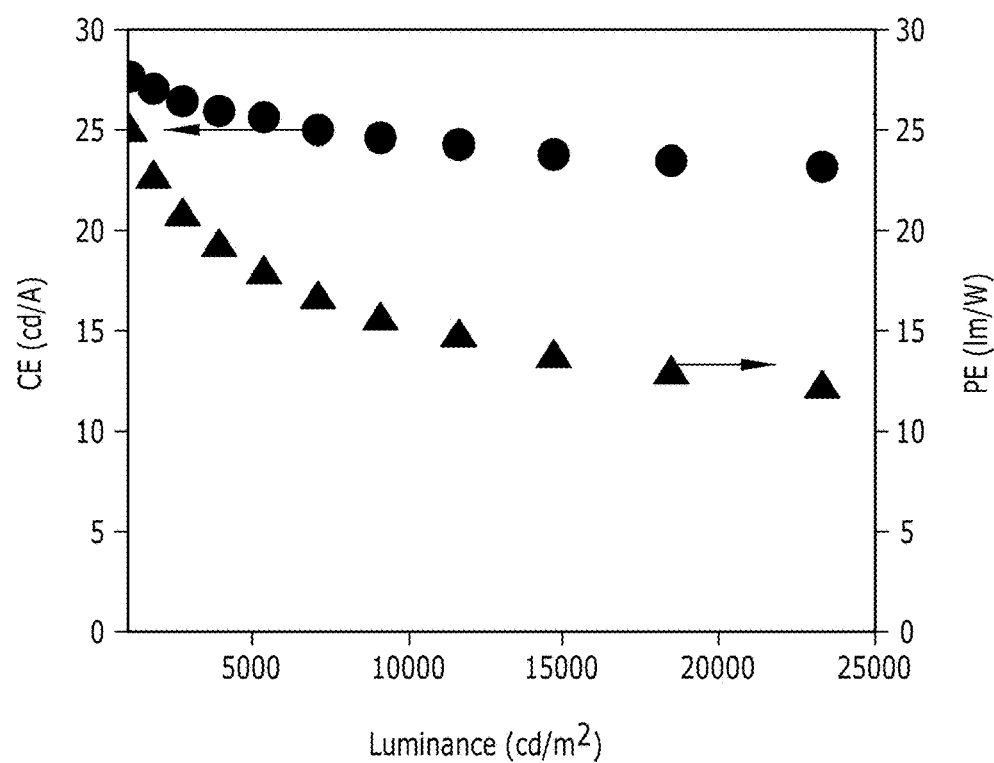
FIG. 10 is a plot of current efficiency (CE) and power efficiency as a function of luminance of Device B, where the value for CE incorporates the external quantum efficiency (EQE).

FIG. 10 is a plot of current efficiency (CE, cd/A) and power efficiency (PE, lm/W) of Device B as a function of luminance (cd/m$^2$).

Figure 11:
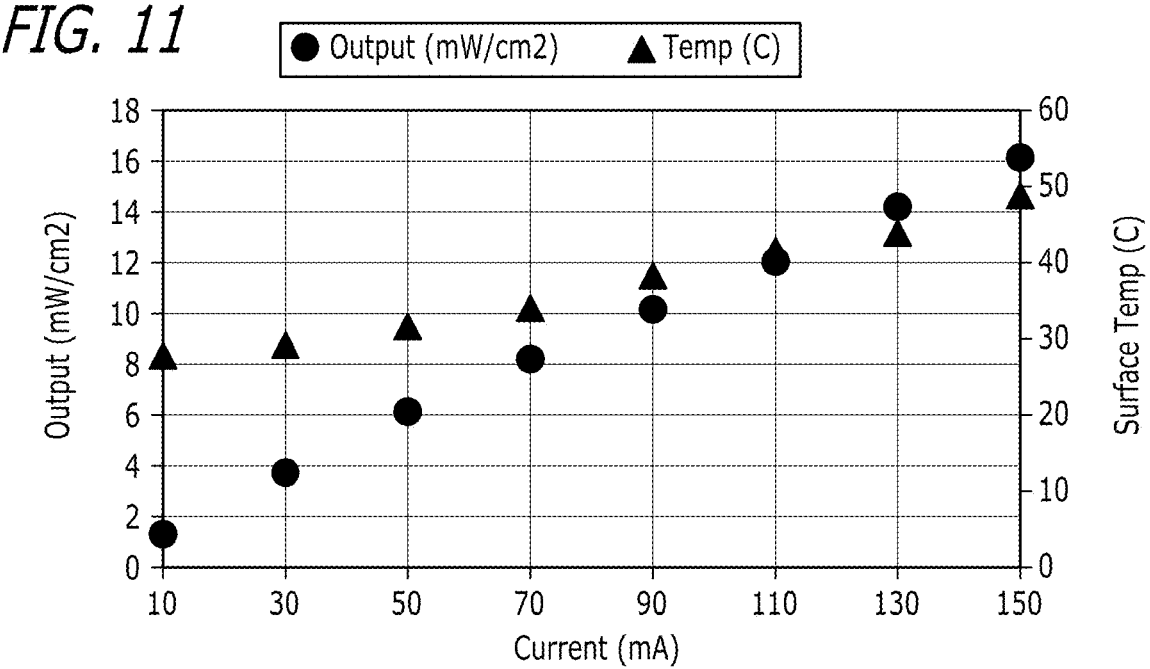
FIG. 11 is a plot of output power and surface temperature as a function of current of Device B.

FIG. 11 is a plot of light output (mW/cm$^2$) and surface temperature (° C.) of Device B as a function of input current (mA). The plot shows that the light output can be 10 mW/cm$^2$ at 90 mA input current, which is sufficient for phototherapy at a luminance range that may be used for that application. The surface temperature at this point is <40° C., and thus can be suitable to apply on or near the skin. The voltage required for 10 mW/cm$^2$ is about 5.5 V, which is suitable for operation with a portable and rechargeable battery. The turn-on voltage for the device was about 2.4 volts and the maximum luminance was about 24,500 cd/m$^2$ with a 1.8 cm$^2$ area device at about 6 V. At 1000 cd/m$^2$ intensity and 623 nm emission, the EQE (external quantum efficiency) was about 17.4%, luminous efficiency was about 27.6 cd/A, and the power efficiency of the device was about 24.8 lm/W.

Device C

Device C was fabricated in a manner similar to the following. The substrate (glass-SiON/Metal foil) was cleaned ultrasonically and sequentially in detergent, water, acetone and then isopropyl alcohol (IPA); and then dried in an oven at about 80° C. for about 30 min under ambient environment. Substrate was then baked at about 200° C. for about 1 hour under ambient environment, then under UV-ozone treatment for about 30 minutes. Soon after UV-ozone treatment, substrates were loaded into a deposition chamber. A reflective bottom anode, e.g., Al (about 100 nm) was deposited at a rate of about 0.1 nm/s. A hole injection layer as dipyrazino[2,3-f:2',3'-h]quinoxaline-2,3,6,7,10,11-hexacarbonitrile (HAT-CN, about 10 nm) was deposited as on reflective anode. NPB (about 50 nm) was then deposited as a hole-transport layer. Bis(1-phenylisoquinoline)(acetylacetonate)iridium (III) ("Ir(piq)$_2$acac") (5 wt %) was co-deposited as an emissive layer with Host-8 material at about 0.01 nm/s and 0.10 nm/s, respectively, to make the appropriate thickness ratio and a total thickness of about 30 nm. 1,3,5-Tris(1-phenyl-1H-benzimidazol-)2-yl)benzene (TPBI, about 50 nm) was then deposited at about 0.1 nm/s rate on the emissive layer. A thin layer of lithium fluoride (LiF, about 1 nm) (electron-injecting material) was deposited at about 0.005 nm/s rate, followed by deposition of the magnesium (Mg, about 1 nm) at about 0.005 nm/s rate. A semi-transparent cathode (about 20 nm) was deposited by co-deposition of magnesium (Mg) and silver (Ag) at a ratio of about 1:3 by weight. Finally a capping layer as MoO$_3$ (about 80 nm) was deposited to enhance light output by micro cavity effect. All the deposition was done at a base pressure of about 2×10$^{-7}$ torr.

Figure 12:
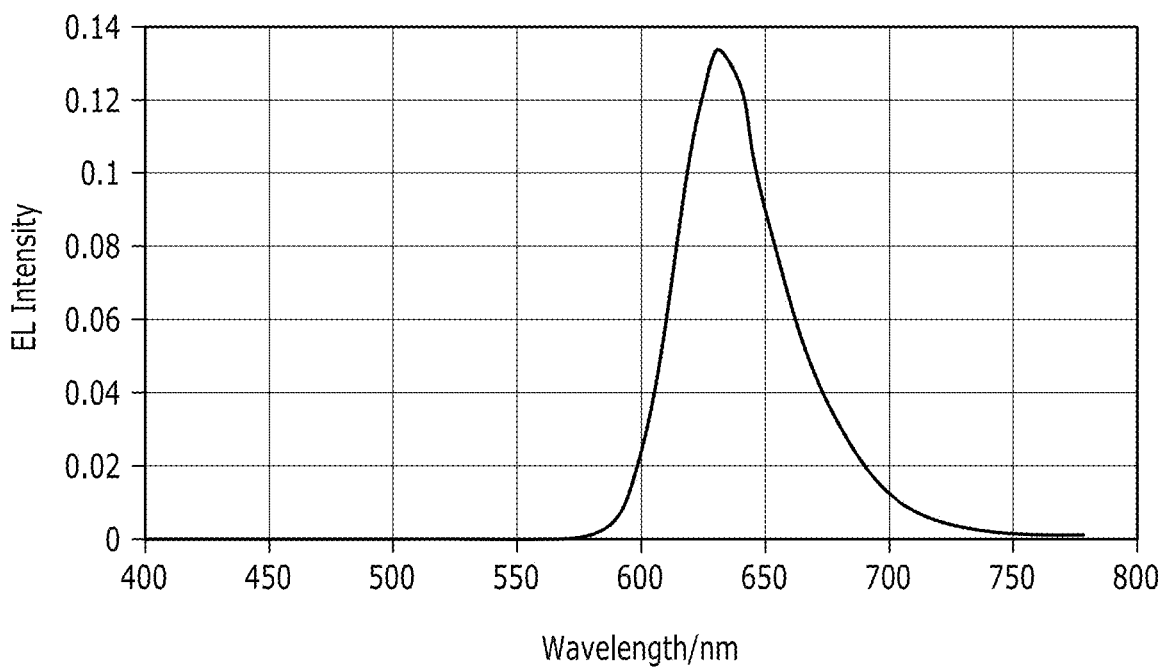
FIG. 12 shows the EL spectrum of Device C.

EL spectra of device C, shown in FIG. 12, was measured with a Spectrascan spectroradiometer PR-670 (Photo Research, Inc., Chatsworth, Calif., USA); and I-V-L characteristics were taken with a Hamamatsu integrated sphere system (Hamamatsu Photonics K. K., Hamamatsu City, Japan, A-10119).

Figure 13:
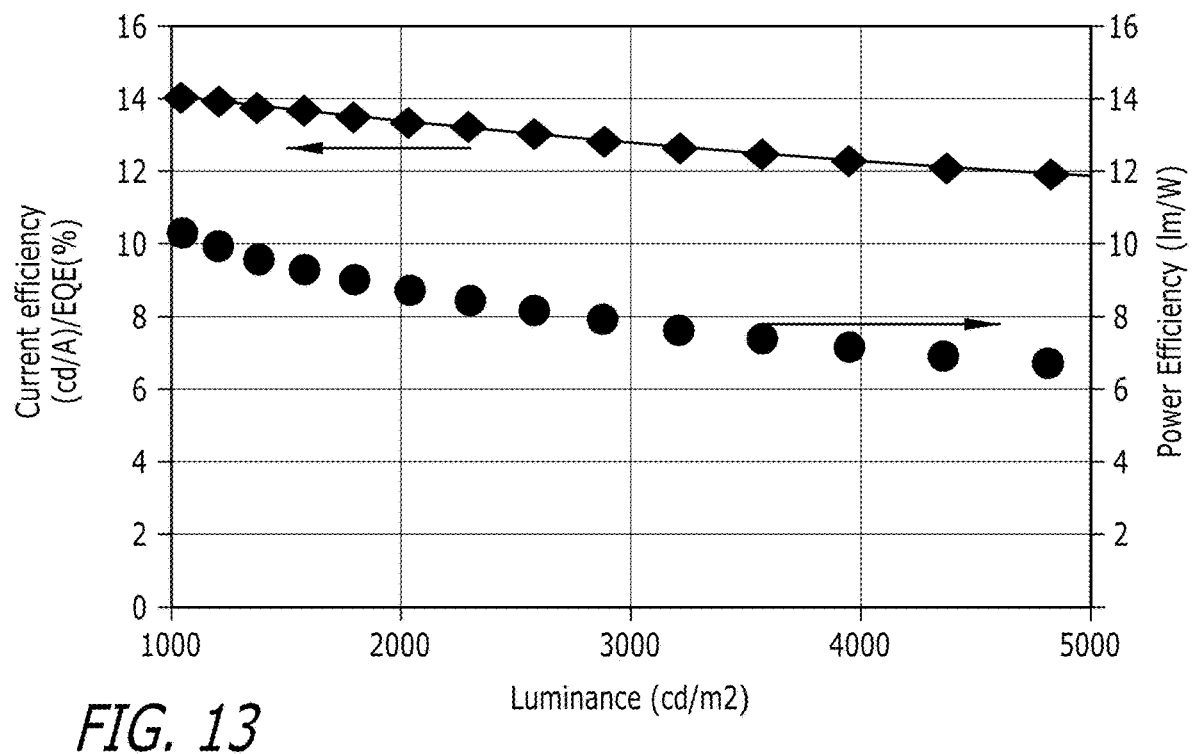
FIG. 13 is a plot of current efficiency and power efficiency as a function of luminance of Device C.

FIG. 13 is a depiction of the current efficiency (diamonds) and power efficiency (filled circles) of Device C as a function of luminance. In FIG. 9, current efficiency is represented by (cd/A)/% external quantum efficiency (EQE). The turn-on voltage for the device was about 2.5 volts and the maximum luminance was about 45,600 cd/m$^2$ with 1.8 cm$^2$ area device at about 8V. The EQE, luminous efficiency and power efficiency of the device at 1000 cd/m$^2$ were about 14.5%, 14.3 cd/A and 10.5 lm/W, respectively, at 630 nm emission.

Figure 14:
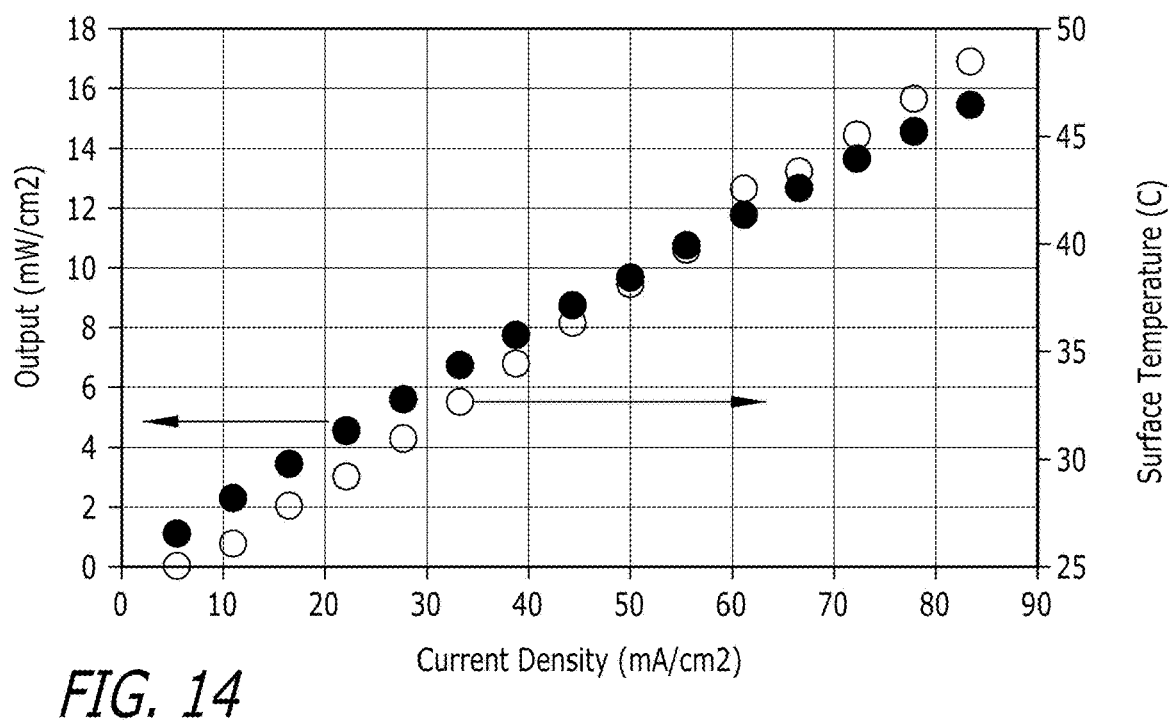
FIG. 14 is a plot of output power and surface temperature as a function of current of Device C.

FIG. 14 is a plot of output power (mW/cm$^2$, filled circles) and surface temperature (° C., open circles) of Device B as a function of current density (mA/cm$^2$). As FIG. 14 indicates, an output of 10 mW/cm$^2$ can be obtained with 50 mA/cm$^2$ current density, suitable for low level light therapy.

Device D

Device D was fabricated in a manner similar to the following. The stainless steel substrate (SUS) was cleaned ultrasonically and sequentially in detergent, water, acetone and then IPA; and then dried in an oven at about 200° C. for about 60 min under ambient environment. A resist material (polysiloxane) was coated on the SUS. The resin was then cured at 200° C. for 1 hour in a clean oven to get a final thickness about 2 um. Substrates were then loaded into a deposition chamber. A reflective bottom anode, which in this example was Al (about 100 nm), was deposited at a rate of about 0.1 nm/s. A hole injection layer of dipyrazino[2,3-f: 2',3'-h]quinoxaline-2,3,6,7,10,11-hexacarbonitrile (HAT-CN, about 10 nm) was deposited as on reflective anode. NPB (about 50 nm) was then deposited as a hole-transport layer. Bis(1-phenylisoquinoline)(acetylacetonate)iridium (III) ("Ir (piq)$_2$acac") (5 wt %) was co-deposited as an emissive layer with Host-8 material at about 0.01 nm/s and about 0.10 nm/s, respectively, to make the appropriate thickness ratio and a total thickness of about 30 nm. 1,3,5-Tris(1-phenyl-1H-benzimidazol-)2-yl)benzene (TPBI, about 50 nm) was then deposited at about 0.1 nm/s rate on the emissive layer. A thin layer of lithium fluoride (LiF, about 1 nm) (electron-injecting material) was deposited at about 0.005 nm/s rate, followed by deposition of the magnesium (Mg, about 1 nm) at a rate of about 0.005 nm/s. A semi-transparent cathode (about 20 nm) was deposited by co-deposition of magnesium (Mg) and silver (Ag) at a ratio of about 1:3 by weight. Finally, a capping layer of MoO$_3$ (about 80 nm) was deposited to enhance light output by microcavity effect. All the deposition was done at a base pressure of about 2×10$^{-7}$ torr.

Figure 15:
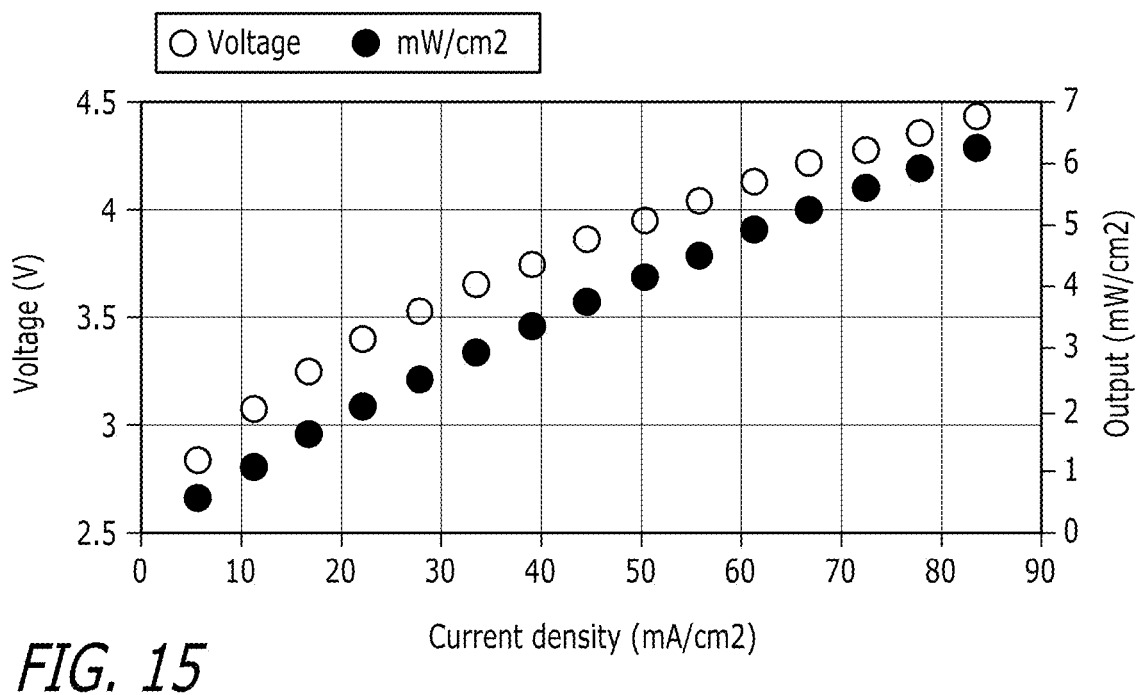
FIG. 15 shows a plot of operating voltage and output power as a function of current density of Device D.

FIG. 15 is a plot of operating voltage (V, open circles) and output power (mW/cm$^2$, filled circles) of Device D as a function of current density (mA/cm$^2$). As FIG. 15 illustrates, an output of 4 mW/cm$^2$ can be obtained with a 50 mA/cm$^2$ current density, which is suitable for low level light therapy.

Example 3: In Vitro Model and Assays

1) In Vitro Hyperglycemic Diabetic Model

Primary Human Dermal Fibroblasts were purchased from American Type Culture Collection (ATCC, Manassas, Va.) and grown in serum-free medium with a glucose concentration of 180 mM as an in vitro hyperglycemic diabetic model. A total of 10,000 cells were seeded in a 4-well chamber slide with final volume of 550 µl and cultured at 37° C., 5% CO$_2$. After cell attachment, cells were subjected to light treatment with different light sources or without any treatment (Control). The length of culture post-treatment was dictated by the bioassays used.

2) Light Treatment

Cells were either treated with an OLED device (630 nm peak wavelength) or laser (635 nm wavelength) at a power density of 7 mW/cm$^2$ or 10 mW/cm$^2$ and fluences of 0.2, 1 or 5 J/cm$^2$. Cells were irradiated through the glass bottom of the chamber slides.

3) Bioassays a. MTS Assay

The Promega Corporation MTS assay (Madison, Wis.) was used. This assay is based on the reduction of tetrazolium salts into formazan, which can be measured colorimetrically. The conversion is believed to be accomplished by reductase enzymes in mitochondria. This assay determines the number of viable cells based on metabolic activity in live cells. When this assay is used with light therapy which can alter cellular metabolism, the data cannot be interpreted as the number of viable cells and is instead interpreted as a change in mitochondrial metabolism.

Forty minutes after light treatment, 55 µl of MTS solution was added to each chamber. After incubation for 1.5 hour at 37° C., 110 µl of solution was transferred from the chamber slide to a transparent 96-well plate for determining light absorption (wavelength 490 nm) using FLUOstar OPTIMA plate reader (BMG Labtech Inc., Cary, N.C.). Blank controls were medium alone with MTS solution.

b. ATP Assay

ATP was detected by an ATPlite kit (Perkin Elmer, Waltham, Mass.). This assay is based on the production of light caused by the reaction of ATP with added luciferase and D-luciferin. The emitted light is proportional to the ATP concentration.

Ten minutes after light treatment, cell lysis solution was added to each chamber and shaken for 5 minutes at room temperature (RT). Substrate solution was added next to each chamber and shaken for another 5 minutes at RT. This mixture was transferred into a white 96-well plate and dark adapted for 10 minutes, the luminescence was determined using FLUOstar OPTIMA plate reader (BMG Labtech Inc., Cary, N.C.).

c. CyQuant Assay

CyQuant assay (Invitrogen, Carlsbad, Calif.) was used as the cell proliferation assay. Since it is a DNA-based assay, the metabolic activity of the cells does not affect the cell number determination.

After light treatment, the cells were incubated for 24 hours. Supernatant was aspirated from each chamber and cells were frozen at −70° C. overnight. The assay was performed according to manufacturer's recommendations. Briefly, cells in a chamber slide were thawed at RT. Then, 500 µl of cell lysis buffer containing CyQuant GR compound was added into each chamber and incubated for 5 minutes at RT. 100 µl of this mixture was transferred into a 96-well black plate for reading at 480 nm excitation/520 nm emission by OPTIMA plate reader (BMG Labtech Inc., Cary, N.C.). The negative control was cell lysis buffer with CyQuant GR compound and the positive control was 0.5 µg/mL λ DNA in cell lysis buffer with CyQuant GR compound.

Results

1) OLED and Laser Treatment Had Comparable Short-Term Effects on Increasing ATP Production and Mitochondrial Metabolism.

Figure 16:
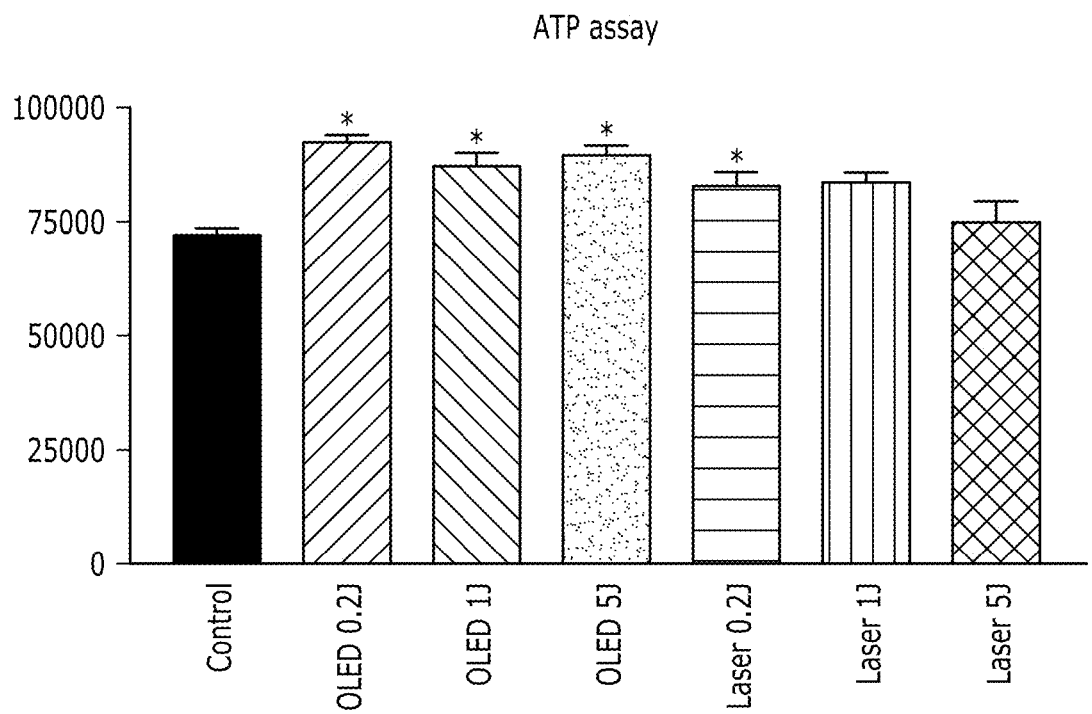
FIG. 16 is a graph depicting mitochondrial metabolism for cells illuminated with OLED or laser light as compared to a control.

Cells were treated with light from an OLED or a laser at a power density of 7 mW/cm$^2$ at fluences of 0.2, 1, or 5 J/cm$^2$. Ten minutes after treatment, the ATP assay was performed. The results are shown in FIG. 16. Cells irradiated with the OLED at a power density of 7 mW/cm$^2$ had statistically significant increases in total ATP levels at the three fluences tested. Out of the three laser groups, only the cells treated with a fluence of 0.2 J/cm² group had a significantly higher total ATP level as compared to the control.

Figure 17:
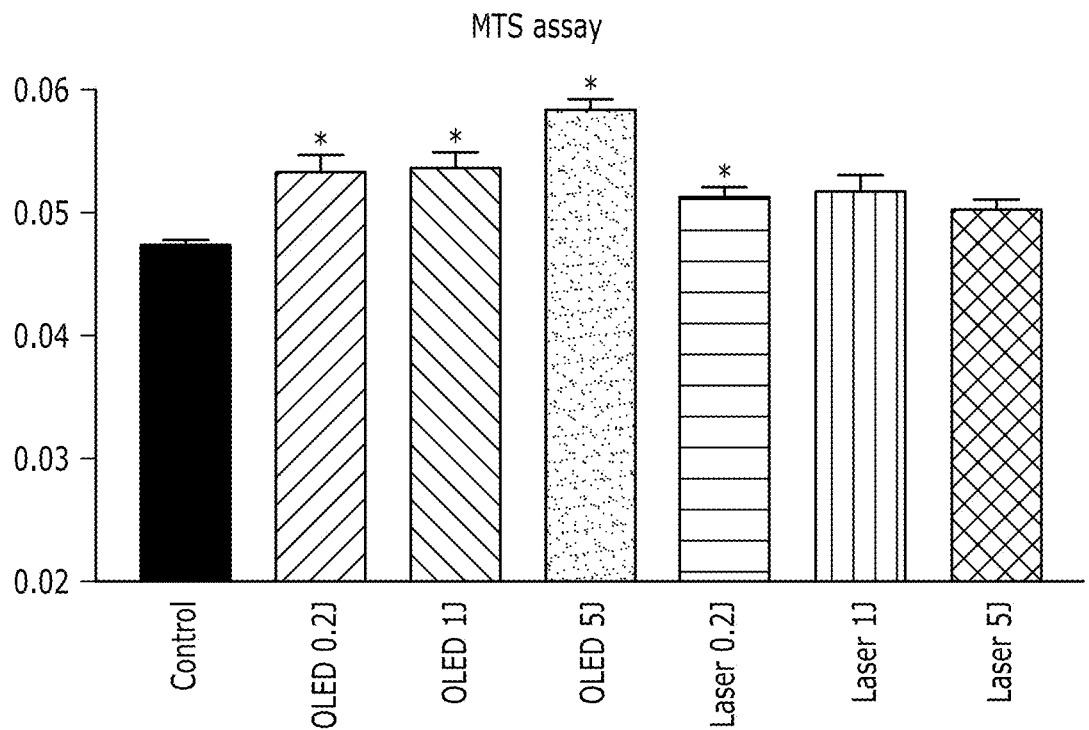
FIG. 17 is a graph depicting the number of viable cells as determined by MTS assay for cells illuminated with OLED or laser light as compared to a control.

Forty minutes after treatment, the MTS assay was performed to determine mitochondrial metabolism. The results are depicted in FIG. 17. OLED groups with three different fluences showed significantly higher mitochondrial metabolism than Control (p<0.05). As seen with the ATP assay, only the cells irradiated with the laser at a fluence of 0.2 J/cm² had a significantly higher mitochondrial metabolism compared to the Control (p<0.05).

2) OLED and Laser Irradiation Had Comparable Effects on Cell Proliferation

Figure 18:
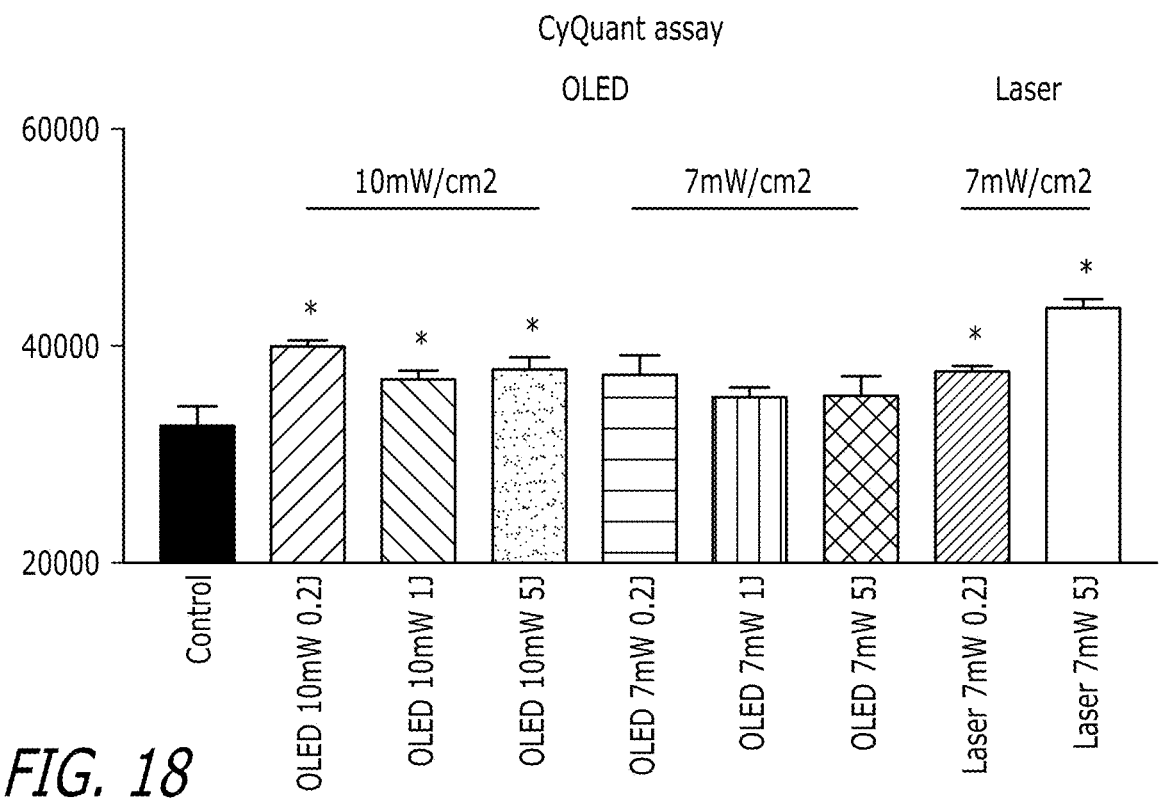
FIG. 18 is a graph depicting cell proliferation for cells illuminated with OLED or laser light as compared to a control.

Cells were treated with OLED irradiation at a power density of 7 mW/cm² or 10 mW/cm² at fluences of 0.2, 1 or 5 J/cm², or with a laser at a power density of 7 mW/cm² at 0.2 or 5 J/cm². Twenty hours after treatment, the CyQuant assay was used to determine cellular proliferation. The results are depicted in FIG. 18. The laser irradiated group (7 mW/cm² at both 0.2 and 5 J/cm²) had significantly higher cell number than Control. OLED irradiated groups (10 mW/cm² at three different fluences 0.2, 1 or 5 J/cm²) also had significantly higher cell numbers.

3) Cellular Changes Caused by the OLED Device were not Due to Heating

To determine if the cellular changes observed after OLED treatment were caused by heat or photobiomodulation, primary human dermal fibroblasts were cultured in a glucose concentration of 180 mM and divided into several groups:
1) Control: No treatment.
2) OLED: Cells were treated with OLED with 7 mW/cm² at 0.2, 1 or 5 J/cm². The treatment times for the fluences tested were 29 seconds, 2 minutes and 23 seconds, and 11 minutes and 54 seconds respectively.
3) Foil-covered (F): Cells were treated the same as OLED groups except the OLED device was covered by a layer of aluminum foil. The foil prevented the light from reaching the cells, but allowed for transfer of 61% of the heat.
4) Hot plate (H): The chamber slides were placed on a hot plate. The temperature of the hot plate was adjusted so that the temperature increase in the chamber slide was the same as that caused by the OLED. The duration of the heat treatment corresponded to the OLED irradiation times for each of the fluences tested.
5) Laser: Cells were treated with a 635 nm wavelength laser with 7 mW/cm² at 0.2 J/cm². Forty minutes after treatment, the MTS assay was performed to measure the mitochondrial activity of cells.

Figure 19:
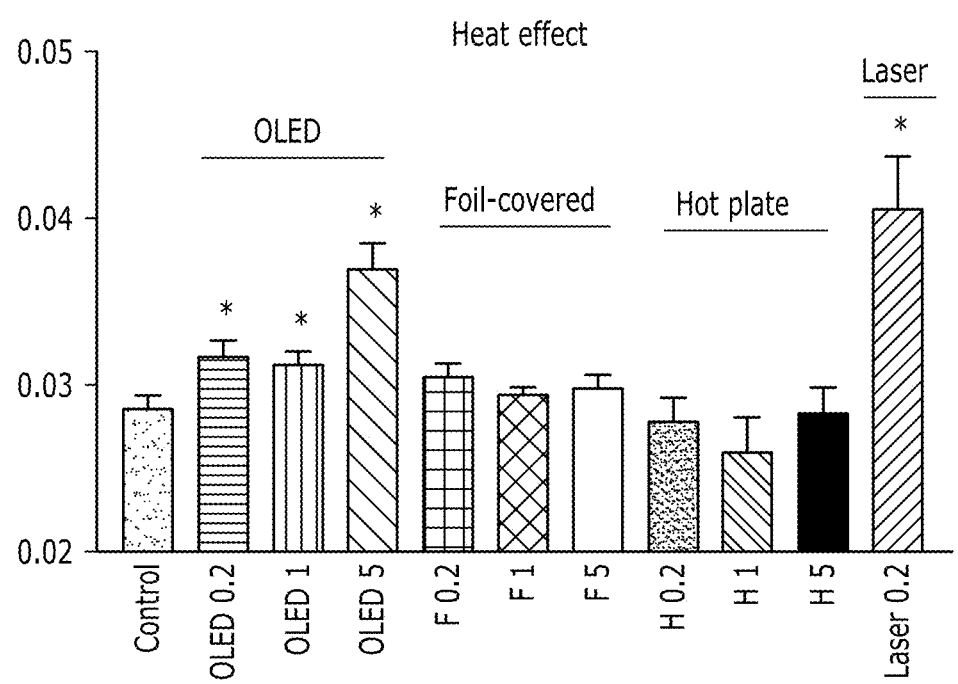
FIG. 19 is a graph depicting the number of viable cells as determined by MTS assay for cells illuminated with OLED or laser light as compared to a controls receiving no light as well as cells heated by hot plate, or by placing a foil over the sample in the presence of the OLED.

Cells treated with OLED irradiation at all fluences and laser irradiation at 0.2 J/cm² showed significantly higher mitochondrial metabolism than Controls. The results are depicted in FIG. 19. When the OLED was covered with foil, the significant increase in the mitochondrial metabolism was eliminated. There was also no significant difference in mitochondrial metabolism between cells treated on the hot plate and the untreated controls. These data establish that the cellular changes caused by irradiation with the OLED device were due to photobiomodulation and not thermal effects.

4) Comparison of OLED and Laser on Mitochondrial Metabolism (MTS Assay), Total ATP Production and Cell Proliferation (CyQuant Assay)

A summary of the results with different light sources for the three bioassays is presented in the Table 1 below. In this table, '+' means statistically significant positive effect; '−' means a statistically significant negative effect (or inhibitory effect); and, NA indicates a parameter that was not tested. A blank cell indicates that no significant difference was seen compared to the hyperglycemic controls.

TABLE 1

|  | Power density (mW/cm²) | Fluence (J/cm²) | MTS | ATP | CyQuant |
|---|---|---|---|---|---|
| OLED | 7 | 0.2 | + | + |  |
|  |  | 1 |  | + |  |
|  |  | 5 | + | + |  |
|  | 10 | 0.2 | + | + | + |
|  |  | 1 | + | + | + |
|  |  | 5 | + |  | + |
| Laser | 7 | 0.2 | + | + | + |
|  |  | 1 |  |  | NA |
|  |  | 5 |  |  | + |
|  | 10 | 0.2 | NA | + |  |
|  |  | 1 | NA |  | NA |
|  |  | 5 | NA | − | NA |

Example 3: In Vivo Wound Healing Study (ZDF LEAN Control Rats)

Eight Zucker Diabetic Fatty (ZDF) LEAN strain (fa/+ phenotype) rats were used in this study. Two full-thickness wounds were made on each study rat, one on the left flank and one on the right, using a sterile 8 mm diameter biopsy punch. Wounds were splinted using MASTISOL® liquid adhesive (Ferndale Laboratories, Ferndale, Mich.) with TEGADERM® HP dressing (3M, Maplewood, Minn.). The wound on the right flank was treated with the OLED device, and that on the left was left untreated, as a control. Irradiation of the wound on the left flank was performed with the OLED device daily for 5 consecutive days. The power density used was either 3.5 or 7 mW/cm², and the total energy density for all was 5 J/cm². The treatment time was 23 min., 49 sec. for the 3.5 mW/cm² group, and 11 min., 54 sec. for the 7 mW/cm² group.

Wound Closure Measurements

Photo images were taken daily of both control OLED-treated flanks. Wound closure area was measured using ImageJ software (a Java-based, public domain image processing program). Percent wound closure on each Day X (i.e., Wound Closure %) was calculated as: 100×[(Area Closure on Day 1)−(Area Closure on Day X)]/(Area Closure on Day 1).

Histological Staining and Score

Figure 23A:
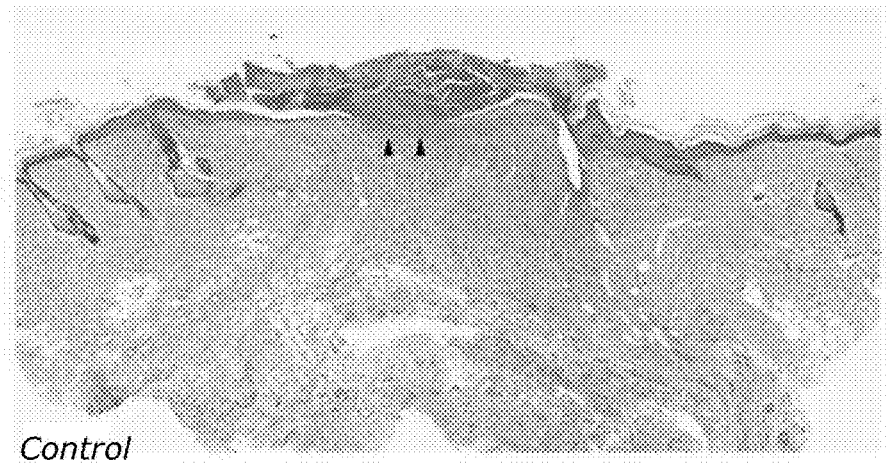
FIGS. 23A-23C show hematoxylin and eosin (H&E) histological staining the epithelium cross-sections of laser- and OLED-treated and control samples.
Figure 23B:
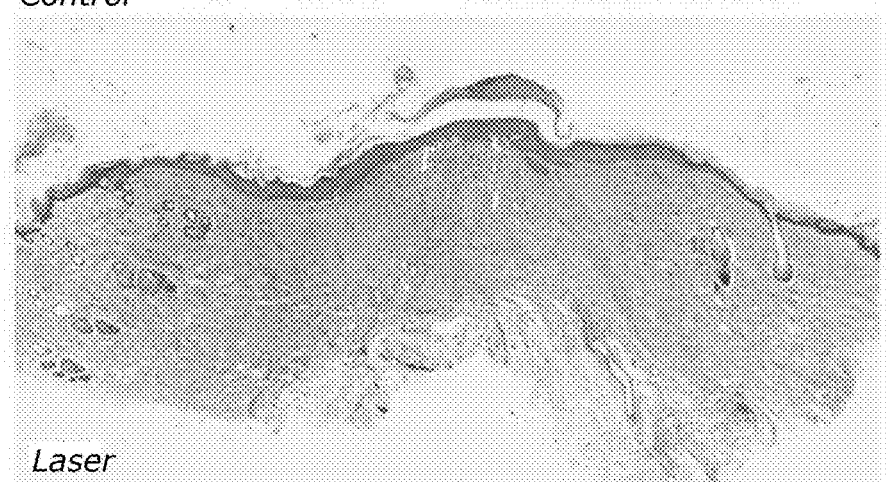
Figure 23C:
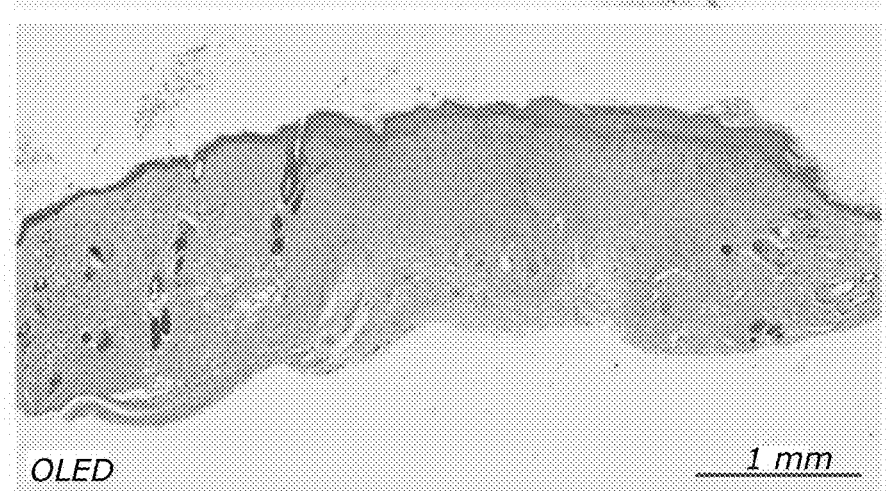

Animals were sacrificed at day 10 post-surgery. Skin samples including the wound area were collected and fixed in 4% paraformaldehyde overnight and then transferred to phosphate buffered saline solution. The wound specimens were divided along the greatest diameter and underwent routine H&E histological staining. See FIGS. 23A-23C. Each section was scored from 1 to 15. This histologic score was based on the degree of re-epithelialization, cellular invasion, granulation tissue formation, collagen deposition, and vascularity according to the criteria in Table 2, as follows.

TABLE 2

| Score | Parameter | Criteria |
|---|---|---|
| 1-3 | Epithelialization | None to very minimal |
|  | Cellular content | None to very minimal (mainly inflammatory cells) |

TABLE 2-continued

| Score | Parameter | Criteria |
|---|---|---|
| | Granulation tissue | None to sparse amount at wound edges |
| | Collagen deposition | None |
| | Vascularity | None |
| 4-6 | Epithelialization | Minimal (less than half of wound diameter) to-moderate (more than half of wound diameter) |
| | Cellular content | Predominantly inflammatory cells, few fibroblasts |
| | Granulation tissue | None to thin layer at wound center, thicker at wound edges |
| | Collagen deposition | Few collagen fibers |
| | Vascularity | Few capillaries |
| 7-9 | Epithelialization | Completely epithelialized; thin layer |
| | Cellular content | More fibroblasts, still with inflammatory cells |
| | Granulation tissue | 7, sparse at wound center, mainly adipose tissue underneath epithelium; 8 thin layer at wound center, few collagen fibers; 9, thicker layer, more collagen |
| | Vascularity | Moderate neovascularization |
| 10-12 | Epithelialization | Thicker epithelial layer |
| | Cellular content | Predominantly fibroblasts |
| | Granulation tissue | Uniformly thick |
| | Collagen deposition | Moderate-to-extensive collagen deposited, but less mature as compared to collagen of unwounded skin margin |
| | Vascularity | Extensive neovascularization |
| 13-15 | Epithelialization | Thick epithelium |
| | Cellular content | Fewer number of fibroblasts in dermis |
| | Granulation tissue | Uniformly thick |
| | Collagen deposition | Dense, organized, oriented collagen fibers |
| | Vascularity | Well defined capillary systems |

Wound Closure Measurements

Figure 20A:
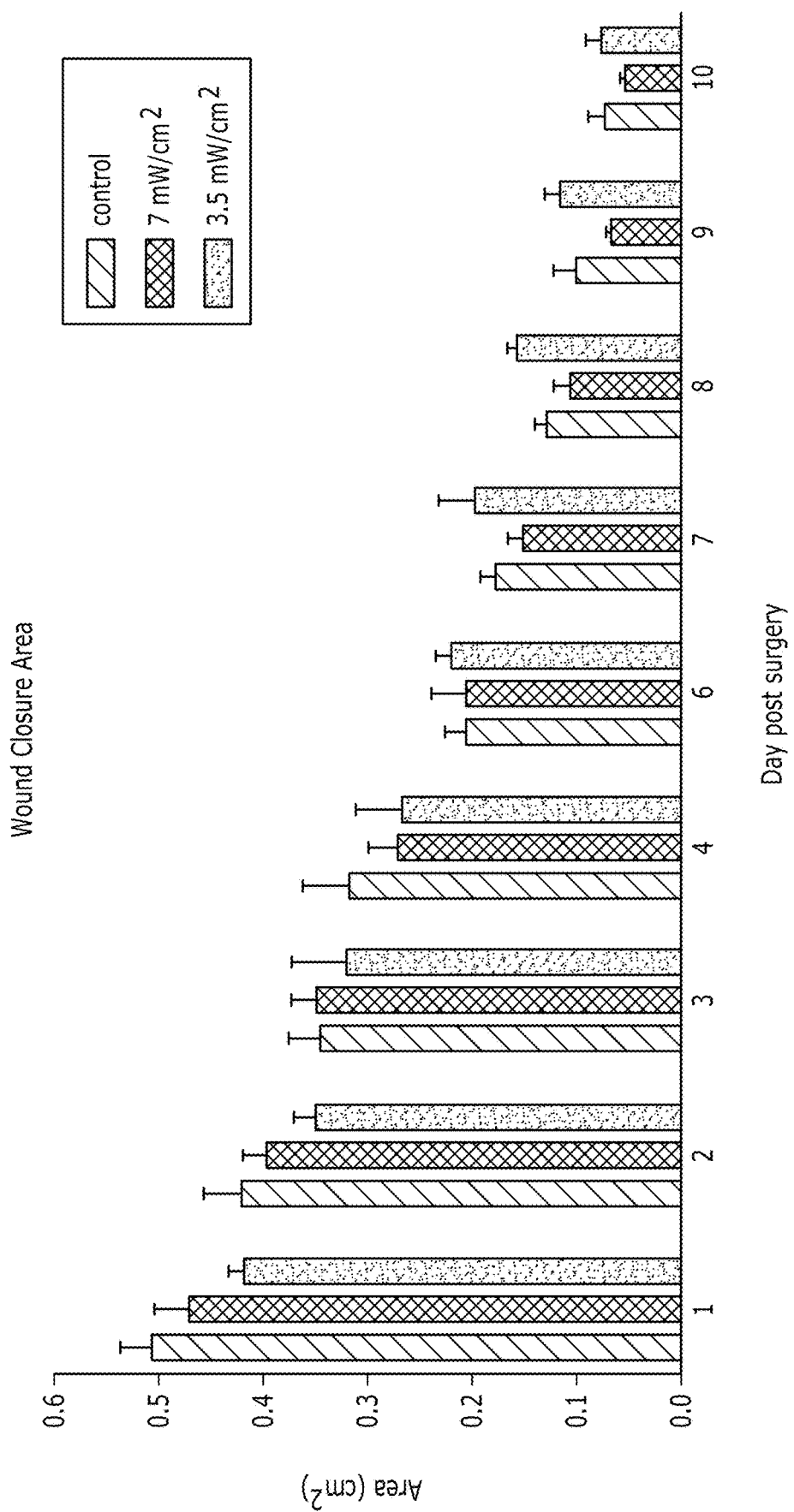
FIGS. 20A and 20B show plots of wound closure by area and percent, respectively, of three test groups: untreated control, and OLED device output power of 3.5 mW/cm$^2$ and 7 mW/cm$^2$.
Figure 20B:
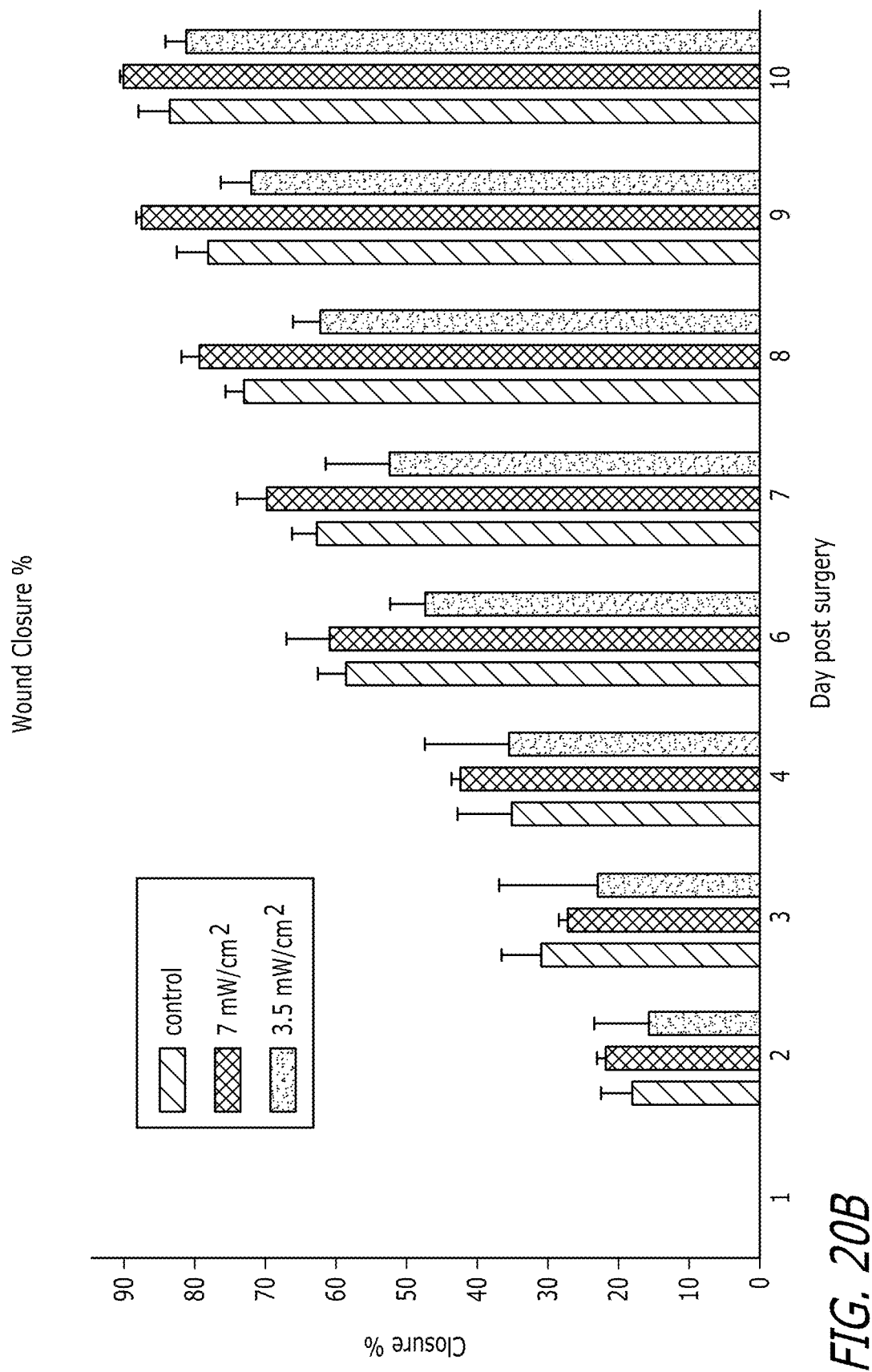

Flank wounds treated with the OLED device at 7 mw/cm$^2$ demonstrated significantly less wound area on Day 8 ($p<0.05$) and Day 9 ($p<0.01$) post-surgery than the wounds treated with the OLED device at 3.5 mW/cm$^2$ (student t-test analysis), although neither of the OLED-treated groups showed a significant difference in wound area when compared to controls (FIG. 20A). There was no significant difference between control and OLED-treated groups in percent wound closure (FIG. 20B).

Example 4: In Vivo Hyperglycemic Diabetic Model

Male ZDF OBESE strain rats homozygotic for the leptin receptor gene deficiency phenotype (fa/fa) can be induced into type II diabetes with a special diet. (Unless otherwise indicated, "ZDF rats" as used herein refers to this ZDF OBESE strain, as distinguished from the control ZDF LEAN strain). The characteristics of ZDF rats are: 1) hyperglycemia, 2) early hyperinsulinemia, 3) fasting hyperglycemia, 4) abnormal glucose tolerance, 5) hyperlipidemia, 6) mild hypertension, 7) impaired wound healing and 8) kidney disease. It is known that wound healing in ZDF rats requires a significantly prolonged closure time compared to normal control rats. See, e.g., JT Vrabec, *Otolaryngol. Head Neck Surg.* (1998), 118(3):304. This is one reason ZDF rats are commonly used as a model for diabetic wound healing.

A total of 30 rats were used in this Example: 8 LEAN controls, 12 OLED-treated OBESE rats, and 10 laser-treated OBESE rats. The LEAN control rats for this model were heterozygotic (fa/+) for the leptin receptor gene and cannot be induced into diabetes when fed with the same diet as the deficient phenotype OBESE rats.

Splinted Wound Model

Maintaining an occlusive dressing over excisional skin wounds in laboratory animals is essential to prevent invasion of microorganisms, to allow experimentally induced wounds to resurface more quickly, and to prevent cross-contamination when irradiating wounds using a contact mode. Uncovered wounds of rats, which are loose-skinned animals, heal mainly by contraction, in which wound margins are drawn inward. Wound contraction is retarded in splinted wounds. Healing of splinted wounds in diabetic rats is through epithelial regeneration and granulation tissue formation, closely mimicking wound healing in human patients with type II diabetes. Therefore, splinted wounds were used in this wound healing example.

Surgery

ZDF rats were anesthetized with isoflurane. The back of each was shaved and depilated by commercial depilatory cream. One full-thickness wound was made on the left and right flank of each rat using a sterile 8 mm diameter biopsy punch. Mastisol adhesive was applied to the skin around the wound margin and allowed to dry for 30 sec. to improve the adhesion of the dressing. Then a Tegaderm HP dressing (44×30 mm) was used to cover the wound. Wounds on the right flank were treated with the OLED device, and those on the left were untreated as controls. The dressing and wounds were monitored daily. When necessary, dressing reattachment or renewal was carried out by applying Mastisol and Tegaderm.

OLED Treatment

A black rubber mask with a hole large enough to expose the wound and surrounding area was placed on the lateral surface of the rat. The wound was centered in the middle of the hole in the mask. Use of the black rubber mask was to assure that light was not scattered or transmitted to the control wound on the opposite site of the rat. The OLED device was placed on top of the mask. There was a separation of about 1 mm between the surface of the OLED device and the wound. Two of the OLED-treated rats were sacrificed at 36 hours after wounding for immunohistochemistry analysis. The other ten rats (3 in the laser-treated group and 7 in the OLED-treated group) were sacrificed at 13 days post-wounding. Irradiation of the wounds was performed immediately after wounding, and daily thereafter for a total of 7 consecutive days. The power density for both light sources was 10 mW/cm$^2$ and the total energy density was 5 J/cm$^2$. The treatment time was 8 min., 20 sec.

For the wound closure measurements, photographic images of the control and light-treated flanks of each rat were taken daily. Wound closure area was measured using ImageJ software. Data obtained in measuring the light-treated flank of each rat was then normalized to its own control (untreated) flank wound.

For histological scoring, skin samples were collected and fixed in 4% paraformaldehyde overnight. Samples were then cut at a 5 μm thickness. The widest section across the wound was selected and stained with H&E. Then, all sections were scanned using the NanoZoomer Digital Pathology scanning system (Institute for Genomic Biology, Urbana, Ill.). Each section was scored with established criteria based on epithelium, cell content, collagen, vascularity and granulation tissue in the wound. See Table 2. Total scores were calculated by summing the scores from all categories.

For immunohistochemistry, skin samples were fixed in 4% paraformaldehyde overnight, then embedded in paraffin and cut at a 5 μm thickness. After deparaffinization, samples were blocked in 8% bovine serum albumen and incubated with ED1 antibody as a primary antibody at 4° C. overnight. ED1 antibody recognizes and attaches to the trans-membrane glycoprotein CD68 on the cell surface of macrophages. Because wound samples were stained with ED1 antibody at 36 hours post-wounding, during the inflammatory phase of wound healing, the antibody effectively acts to label any macrophages present in the inflammatory phase. After washing unbound ED1 antibody from the samples, the tissues were then incubated with secondary anti-ED1 antibody conjugated with ALEXA FLUOR® 488 (Life Technologies, Carlsbad, Calif.), a fluorescent marker. The slides were washed and cover slipped. For quantification of immunolabeling, images were captured digitally and analyzed with ImageJ software. Positive labeling area was identified by establishing a threshold level above background fluorescence, and labeled area was measured in pixels.

Wound Closure Measurement

Figure 21A:
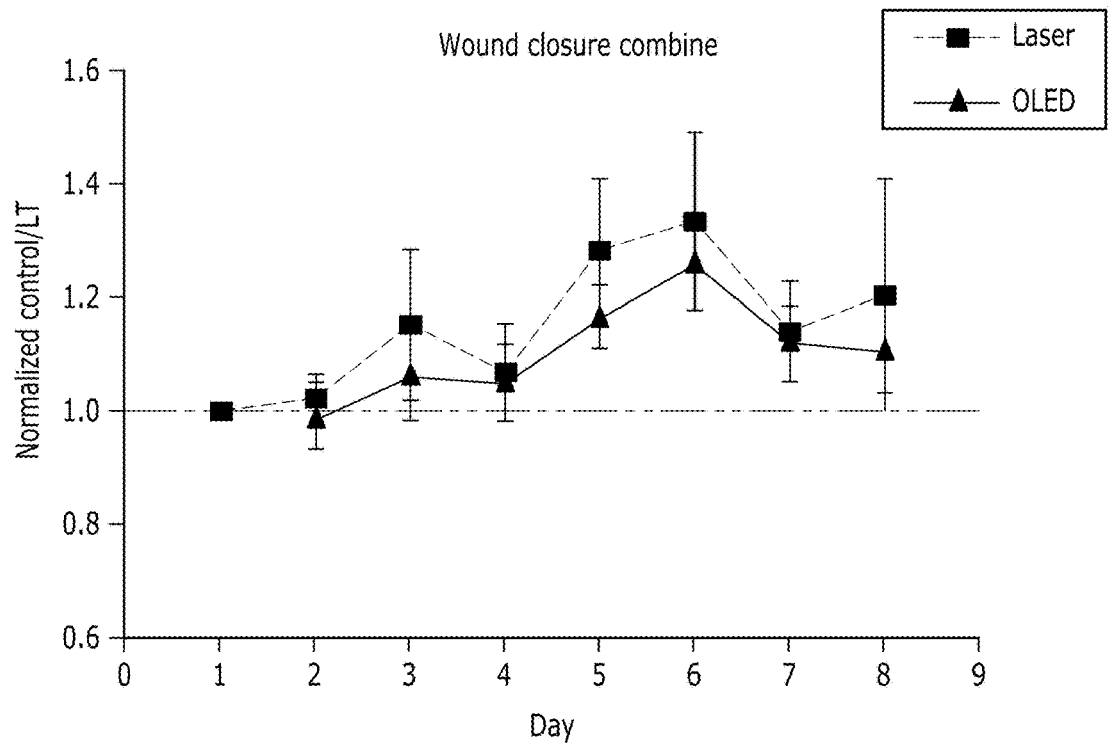
FIGS. 21A and 21B show plots of wound closure measurements.
Figure 21B:
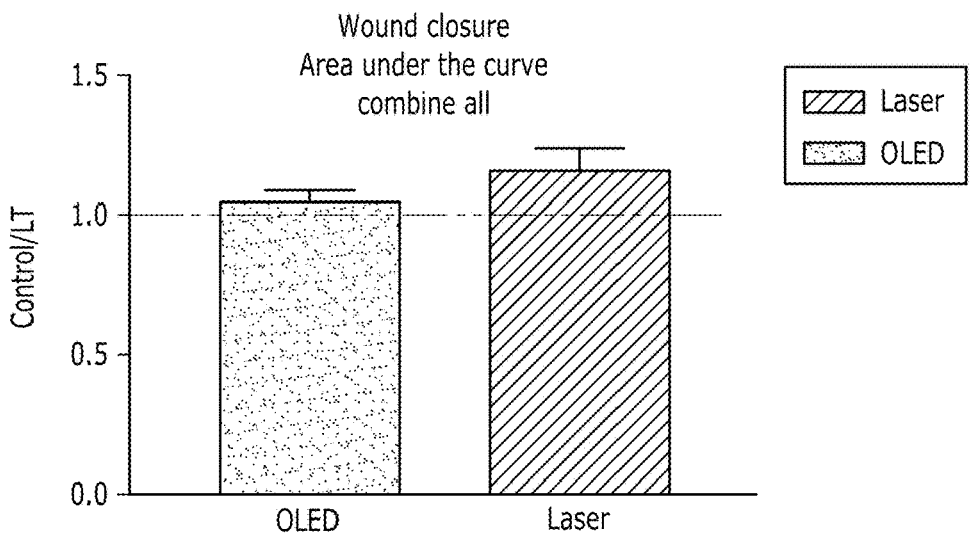

Measurement of LT wound closure in this Example is represented by daily closure measurements (FIG. 21A), or the area under the curve (FIG. 21B), which represents an integrated measurement of the effect of treatment. Each LT wound measurement was normalized to the rat's own control flank would, calculated by control/LT. Accordingly, a value greater than 1 indicates the control flank wound has a larger area than the LT wound, and thus indicates effective light treatment of the wound and better wound healing than in control. Both OLED and laser treatment improved the wound healing in diabetic rats, as shown in FIGS. 21A-21B, as the mean measurements were greater than 1. There was no significant difference between the laser and OLED groups in the efficacy of these devices to support wound closure.

Histological Score

Due to the complexity of the wound healing process, specific criteria were established for scoring wound healing based on parameters involved in the various processes of wound healing, each criterion having assigned numeric values. The strength of this system is that the wound can thus be graded for each parameter separately. The wound parameters, criteria and their values are shown in Table 3 as follows.

TABLE 3

Criteria for Scoring Cutaneous Wound Healing in Rats

| Parameter | Criteria | Value |
| --- | --- | --- |
| Epithelialization | None | 0 |
| | Minimal (less than half the wound area) | 1 |
| | Moderate (more than half the wound area) | 2 |
| | Complete (thin: one or two cells) | 3 |
| | Complete and Thick (more than 2 cells) | 4 |
| Cellular Content | No to few inflammatory cells | 0 |
| | Predominantly inflammatory cells | 1 |
| | Predominantly fibroblasts | 2 |
| | Fewer, mature fibroblasts | 3 |
| Collagen Deposition | None | 0 |
| | Few collagen fibers | 1 |
| | Moderate and immature collagen fibers | 2 |
| | Extensive collagen fibers, but immature compared to unwounded area | 3 |
| | Dense collagen, organized like unwounded areas | 4 |
| Vascularity | None | 0 |
| | Beginning of neovascularization | 1 |
| | Extensive neovascularization | 2 |
| | Vessels more like unwounded area | 3 |
| Granulation Tissue | None to small amount at wound edges | 0 |
| | Forming collagen does not reach wound surface; primarily inflammatory cells below wound surface | 1 |
| | Forming collagen does not reach wound surface; primarily fibroblasts below wound surface; areas (islands) of inflammatory cells | 2 |
| | Forming collagen does not reach wound surface; primarily fibroblasts below wound surface; no areas (islands) of inflammatory cells | 3 |
| | Forming collagen reaches wound surface; primarily fibroblasts below wound surface; and, granular tissue is homogeneous below wound surface (no areas or islands of inflammation) | 4 |
| | Collagen is mature and oriented like unwounded area; fewer fibroblasts | 5 |

Samples were scored from the current study and also the previous study since the criteria were modified after previous study. The total histological score and score for each category are shown in FIGS. 22A-22F. Current data was combined with data from the previous 13 days. The animals used in this Example were all sacrificed on day 13 after wounding. Therefore, only the 13 days' data from the previous study was combined with current data; 8 days' data was excluded.

Histological Staining

Selected cross-sections of skin samples from the three test groups, with H&E histological staining, are also shown. See FIGS. 23A-23C. Note that there is a gap on the epithelia layer (arrowheads) in the Control sample, while the Laser and OLED samples had complete, full epithelium.

Immunohistochemistry of Macrophages

Macrophages play an important role in wound healing. Other than wound debridement, macrophages are known to also secrete cytokines and growth factors to activate and recruit other cell types at the subsequent stages of wound healing and depletion of macrophages results in a significant delay of wound healing. Insufficient classical macrophage activation has been shown in the early stage of wound healing in diabetic wounds (M. Miao et al., *Wound Repair Regen.* (2012) 20(2):203-13). However, prolonged inflammatory phase in diabetic wounds often causes delayed healing (M P Rodero et al., *Int. J. Clin. Exp. Pathol.* (2010) 3(7):643-53).

Figure 24C:
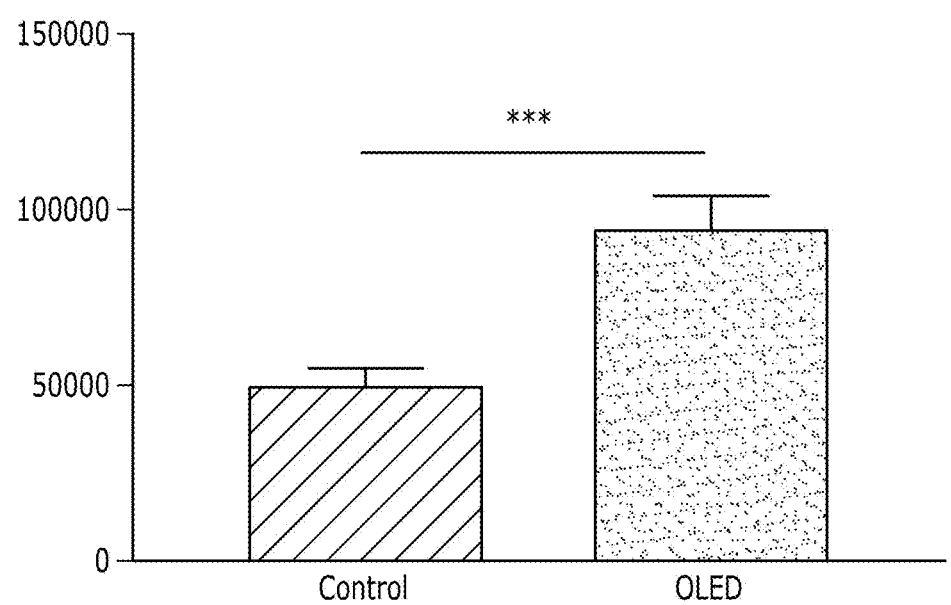

ED1 antibody labels the macrophages during the wound healing process. Significantly more intense macrophage labeling was demonstrated in OLED-treated wounds (FIG. 24B) than in controls (FIG. 24A). Quantification of these images indicated that statistically higher macrophage response was seen in the OLED group than Control ($p<0.001$, FIG. 24C).

Immunohistochemistry of FGF2

FGF2 has a number of effects during wound healing, including for example causing an increase in keratinocyte migration and proliferation, and recruitment of inflammatory cells. FGF2 also stimulates endothelial cell proliferation and neovascularization. Studies have shown that FGF2 knockout mice exhibit delayed wound healing. See, e.g., S. Ortega et al., *Proc. Natl. Acad. Sci. USA* (1998), 95(10): 5672. In diabetic wounds, FGF2 expression is reduced. Accordingly, in this Example the immunohistochemistry of FGF2 was examined in skin from OLED-treated and control wounds in the diabetic rats, to determine whether OLED-treated wounds showed differential FGF2 expression compared to untreated controls.

Figures 25A, 25B:
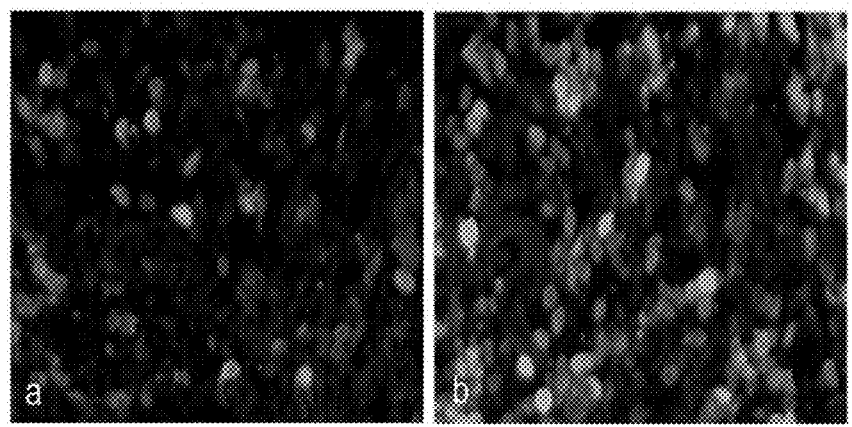
FIGS. 25A-25C show the anti-fibroblast growth factor 2 (FGF2) antibody immunohistochemistry of skin samples in control (FIG. 25A) and OLED-treated (FIG. 25B) groups.
Figure 25C:
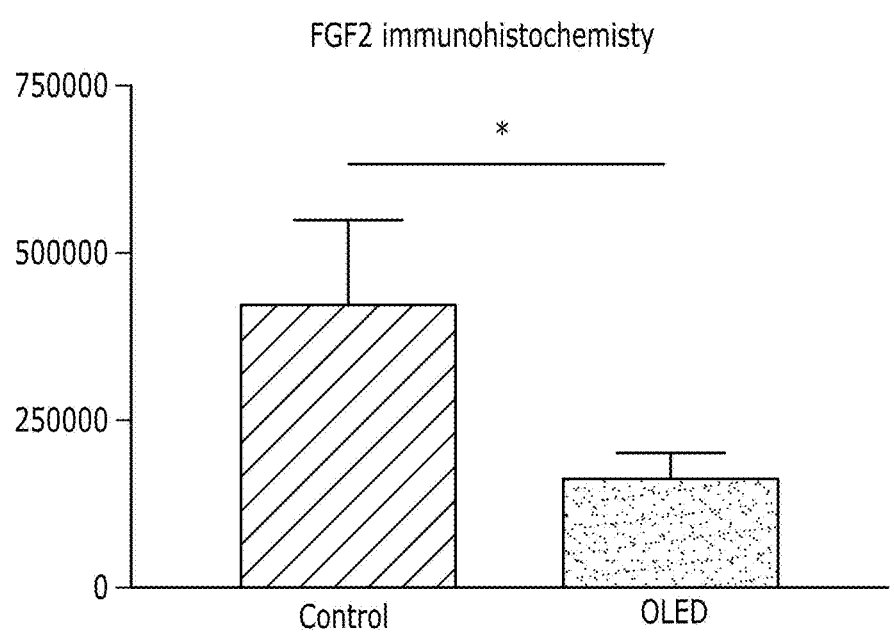

Skin samples were fixed in 4% paraformaldehyde overnight, then embedded in paraffin and cut at a 5 µm thickness. After deparaffinization, samples were blocked in 10% goat serum with 0.1% Triton X and incubated with mouse anti-fibroblast growth factor 2 (FGF2) antibody at 4° C. overnight. The primary FGF2 antibody was washed off the sample, and the tissues were then incubated with goat anti-mouse secondary antibody conjugated with Alexa Fluor 488. The slides were washed and cover slipped. For quantification of immunolabeling, images were captured digitally and analyzed with ImageJ software. Positive labeling area was identified by establishing a threshold level above background and the labeled area was measured in pixels. Results are shown in FIGS. 25A-25C, and indicate that OLED-treated wounds (FIG. 25B) had a significantly higher level of FGF2 expression than the controls (FIG. 25A, $p<0.05$).

SUMMARY

Figure 22A:
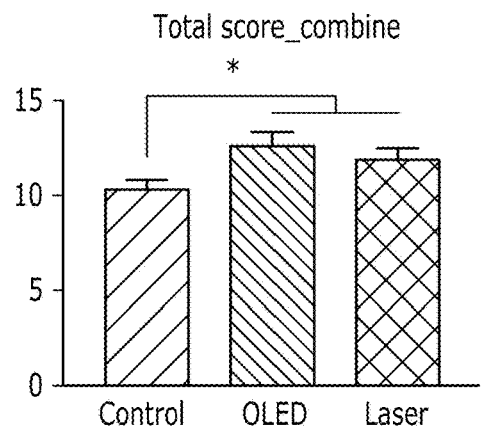
FIGS. 22A-22F chart the histological scores for wound healing in the test groups (Control, OLED-treated and Laser-treated), with scoring based on the criteria shown in Table 2. Control: n=13; OLED: n=7; Laser: n=6. Student's t-test was used to compare between two groups. *p<0.05, **p<0.01.
Figure 22B:
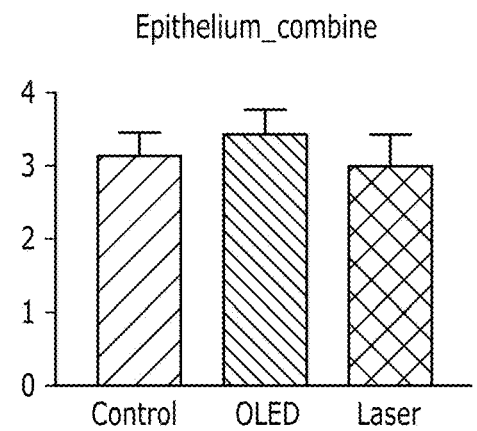
Figure 22C:
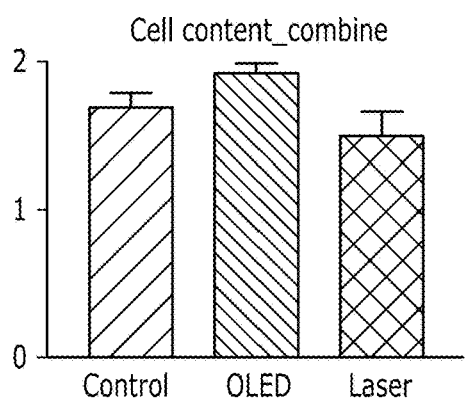
Figure 22D:
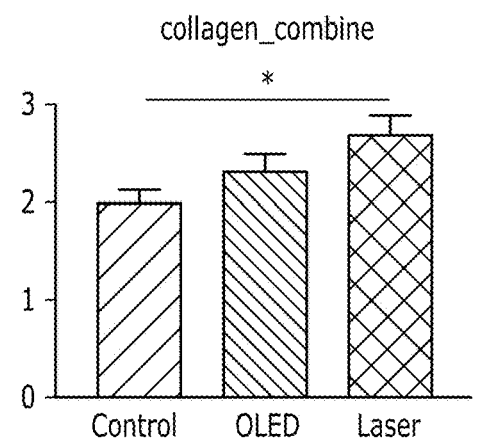
Figure 22E:
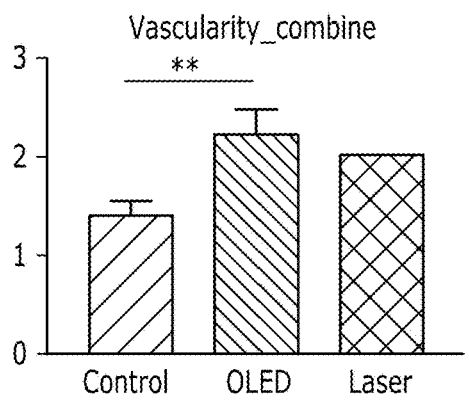
Figure 22F:
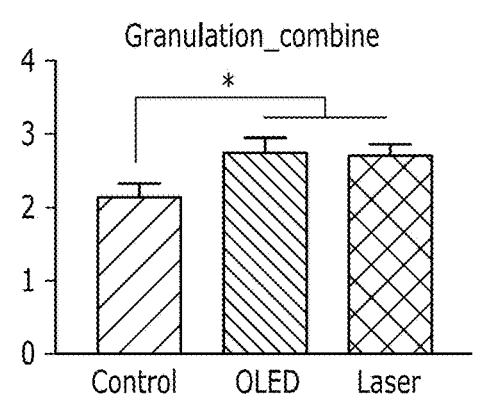

A similar level of effect was found between laser- and OLED-treated groups in wound closure rate. Both laser- and OLED-treated wounds had significantly higher overall histological scores than controls. No statistical difference was seen between OLED- and laser-treated wounds (FIG. 22A). When measurements were separately evaluated by wound healing parameter, there was no difference in epithelialization (FIG. 22B) and cell content (FIG. 22C) values between all treatment groups. However, there was a significantly higher amount of collagen deposition in the laser-treated wounds compared to controls (FIG. 22D). Such significance was not seen between OLED-treated and control wounds. For vascularity, OLED treatment showed a greater positive effect over controls than laser treatment (FIG. 22E). For granulation, both OLED- and laser-treated wounds showed significantly higher values than controls, while no difference was seen between the OLED- and laser-treated wounds (FIG. 22F). Because the total histological score for wound healing was comparable between OLED- and laser-treated groups, while individual parameter scores differed, this suggests the two treatment methods may promote different aspects of wound healing. For example, there may be differential up-regulation of specific factors within the wound. As one example, the OLED treatment appears to promote vascularity in wound healing (FIG. 22E).

Histological staining of wound epithelia indicated healthier epithelium in laser- and OLED-treated wounds: there was a gap in the untreated wound epithelia, while laser- and OLED-treated wounds had complete, full epithelium.

OLED treatment enhanced macrophage activation over controls during the initial stage of wound healing. This suggests that OLED treatment differentially affects macrophage activation, which occurs in the early stages of wound healing, and thus promotes wound healing. This enhancement suggests a potential specific application of OLED for wound healing.

OLED-treated wounds had a significantly higher level of FGF2 expression than the controls (FIGS. 25A-25C). This result is comparable with previous studies using the Fat Sand Rat, in that laser irradiation (632 nm wavelength) promoted FGF2 expression in the diabetic wound. See KR Byrnes et al., Photomed. Laser Surg. (2004), 22(4):281.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A light-emitting device for use in phototherapy comprising:

an anode;
a cathode; and
an organic light-emitting layer disposed between the anode and the cathode;
wherein the organic light-emitting-layer comprises an organic luminescent compound and a host;
wherein the organic luminescent compound is an iridium compound and has a peak emission between 620 nm and 640 nm;
wherein the device is configured to provide an amount of light from the light-emitting layer effective to treat a wound of a human with impaired wound healing resulting from diabetes; and
wherein the host is:

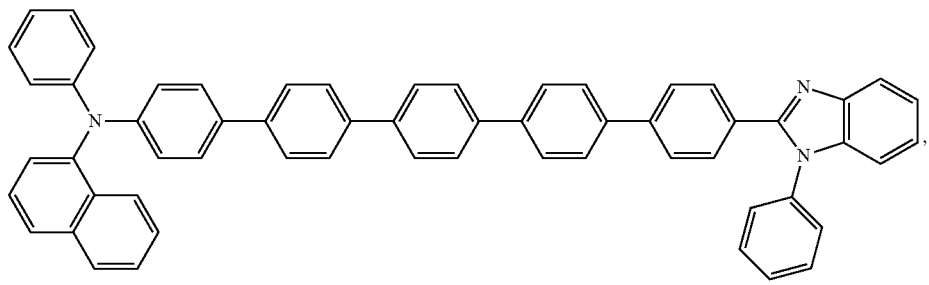

,

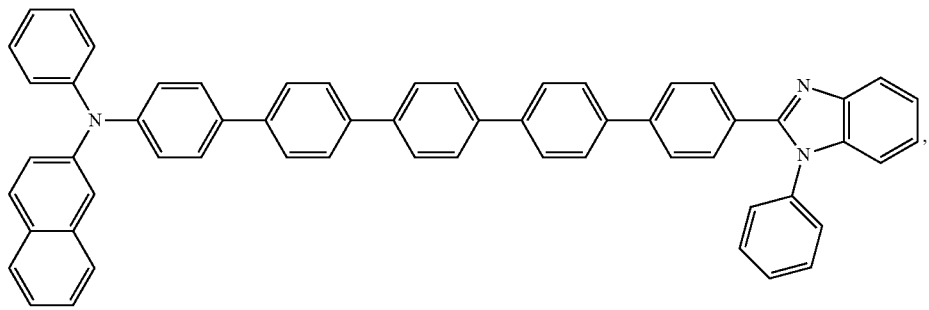

,

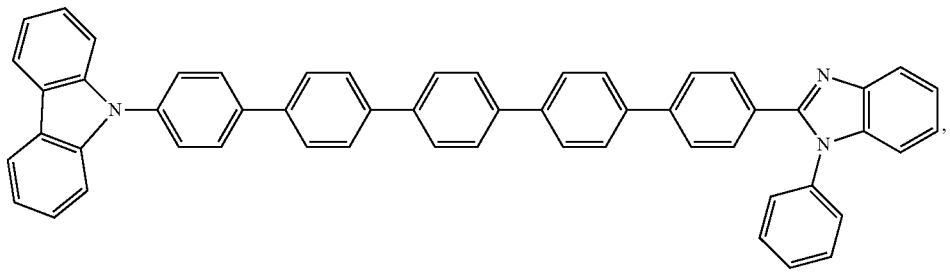

,

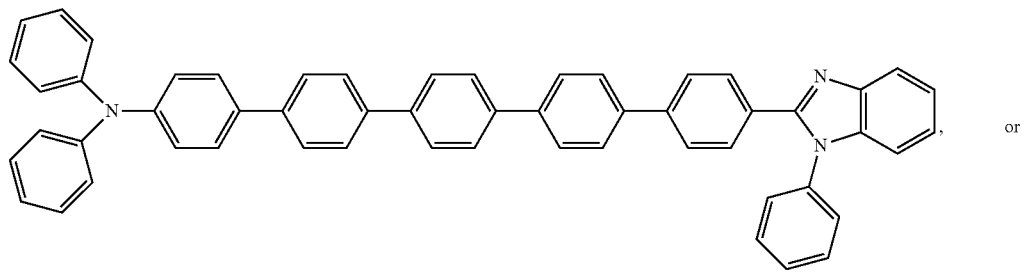

, or

-continued

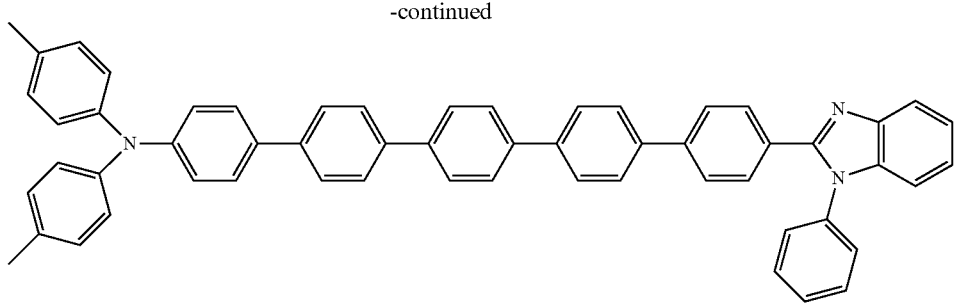

and wherein the device further comprises a dosage component comprising a timer coupled to a positioning component, wherein said dosage component is configured to deliver a light dose of 0.05 J/cm² to 15 J/cm² to a wound.

2. The device of claim 1, wherein the device is configured to provide light to the wound at a power density of 2 mW/cm² to 20 mW/cm².

3. The device of claim 1, wherein the device is configured to provide light to the wound at a power density of 7 mW/cm² to 10 mW/cm².

4. The device of claim 1, wherein the device comprises a flexible substrate, and wherein the light-emitting layer comprises an organic light-emitting diode coupled to the flexible substrate.

5. The device of claim 1, further comprising a capping layer disposed on the cathode.

6. A phototherapy system comprising:
a device according to claim 1; and,
a wound dressing comprising a flexible wrapping material and a hydrocolloid layer;
wherein the device of claim 1 is at least partially positioned between the flexible wrapping material and the hydrocolloid layer.

7. The phototherapy system of claim 6 wherein the dosage component is configured to deliver a light dose of 0.2 J/cm² to 5 J/cm² to the wound.

8. The phototherapy system of claim 6, wherein the wound dressing comprises a hydrocolloid layer that is in direct contact with the device, wherein the phototherapy system is configured so that the hydrocolloid layer is disposed between the device and a wound when the phototherapy system is used to treat the wound.

9. The phototherapy system of claim 8, further comprising an adhesive layer, wherein the phototherapy system is configured so that the adhesive layer is disposed between, and in contact with the, wound and the hydrocolloid layer when the phototherapy system is used to treat the wound.

10. A method of treating a wound comprising: exposing at least a portion of a wound to light from a system of claim 6.

11. The method of claim 10, wherein a light dose of 1 J/cm² to 5 J/cm² is delivered to the wound.

12. The method of claim 10, wherein a light dose of 5 J/cm² is delivered to the wound.

13. The method of claim 10, wherein the wound is treated from 2 days to 8 days after an injury.

* * * * *